US006271357B1

(12) United States Patent
Cook et al.

(10) Patent No.: US 6,271,357 B1
(45) Date of Patent: Aug. 7, 2001

(54) OLIGONUCLEOTIDE MIMICS HAVING NITROGEN-CONTAINING LINKAGES

(75) Inventors: Phillip D. Cook, Carlsbad; Yogesh S. Sanghvi, Encinitas, both of CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/118,654

(22) Filed: Jul. 17, 1998

Related U.S. Application Data

(63) Continuation of application No. 08/180,124, filed on Jan. 11, 1994, now Pat. No. 5,783,862, which is a continuation-in-part of application No. 08/039,979, filed on Mar. 30, 1993, now abandoned, and a continuation-in-part of application No. 08/039,846, filed on Mar. 30, 1993, now abandoned, and a continuation-in-part of application No. 08/040,933, filed on Mar. 31, 1993, now abandoned, and a continuation-in-part of application No. 08/040,903, filed on Mar. 31, 1993, now Pat. No. 5,386,023, and a continuation-in-part of application No. 08/040,526, filed on Mar. 31, 1993, now Pat. No. 5,489,677, each is a continuation-in-part of application No.PCT/US92/04294, filed on May 21, 1992, and a continuation-in-part of application No. 07/903,160, filed on Jun. 24, 1992, now abandoned, which is a continuation-in-part of application No. 07/703,619, filed on May 21, 1991, now Pat. No. 5,378,825, which is a continuation-in-part of application No. 07/566,836, filed on Aug. 13, 1990, now Pat. No. 5,223,618, and a continuation-in-part of application No. 07/558,663, filed on Jul. 27, 1990, now Pat. No. 5,138,045.

(51) Int. Cl.$^7$ .......................... C07H 21/02; C07H 21/04; C07H 21/00

(52) U.S. Cl. .................. 536/23.1; 536/24.31; 536/34.33; 536/24.5; 536/25.3

(58) Field of Search ............................... 536/23.1, 24.31, 536/34.33, 24.5, 25.3

(56) References Cited

U.S. PATENT DOCUMENTS

| 3,687,808 | 8/1972 | Merigan et al. ........................ 195/28 |
| 5,142,047 | 8/1992 | Summerton et al. ................. 544/118 |
| 5,264,562 | 11/1993 | Matteucci ............................ 536/23.1 |
| 5,489,677 | 2/1996 | Sanghvi et al. ...................... 536/22.1 |

FOREIGN PATENT DOCUMENTS

| WO 86/05518 | 9/1986 | (WO) . |
| WO 92/02534 | 2/1992 | (WO) . |
| WO 92/03568 | 3/1992 | (WO) . |
| WO 93/18052 | 9/1993 | (WO) . |

OTHER PUBLICATIONS

Abdel–Magid et al., "Reduction Amination of Aldehydes and Ketones by Using Sodium Triacetoxyborohydride", *Tetra. Lett.*, 1990, 31(39), 5595–5598.

Augustyns, et al., "Influence of the incorporation of (S)–9–(3,4–dihydroxy–butyl)adenine on the enzymatic stability and base–pairing properties of oligodeoxynucleotides", *Nucl. Acids Res.*, 1991, 19(10), 2587–2593.

Cho et al., "An Unnatural Biopolymer", *Science*, 1993, 261, 1303–1305.

Cormier et al., "Synthesis of hexanucleotide analogues containing diisopropylsilyl internucleotide linkages", *Nucl. Acids Res.*, 1988, 16(10), 4583–4594.

Debart et al., "Intermolecular Radical C–C Bond Formation: Synthesis of a Novel Dinucleoside Linker for Non–anionic Antisense Oligonucleosides", *Tetra. Lett.*, 1992, 33(19), 2645–2648.

Egholm et al., "Peptide Nucleic Acids (PNA). Oligonucleotide Analogues with an Achiral Peptide Backbone", *J. Am. Chem. Soc.*, 1992, 114, 1895–1897.

Giannis et al., "Fragmentation and Wittig Olefination of Glucosamine Derivatives—A Simple Route to Open Chain Amino Sugars and Chiral Glycerols", *Tetra. Lett.*, 1988, 44(23), 7177–7180.

Goodchild, "Conjugates of Oligonucleotides and Modified Oligonucleotides: A Review of their Synthesis and Properties", *Bioconj. Chem.*, 1990, 1(3), 165–187.

Greene and Wuts (Eds.), "Protection for the Carbonyl Group", *Protection Groups in Organic Synthesis*, John Wiley & Sons, Inc., 1991, 175–223.

Hanvey, et al., "Antisense and Antigene Properties of Peptide Nucleic Acids", *Science*, 1992, 258, 1481–1485.

Hart et al., "Bis(trimethylstannyl)Benzopinacolate–Mediated Intermolecular Fee–Radical Carbon–Carbon Bond–Forming Reactions: A New One–Carbon Homologation", *J. Am. Chem. Soc.*, 1988, 110, 1631–1633.

Halford and Jones, "Synthetic Analogues of Polynucleotides", *Nature*, 1968, 217, 638–640.

Hillgartner et al., "Bis(trimethylzinn)benzpinakolat, seine reversible Radikalische Dissoziation und Reaktionen", *Liebigs Ann. Chem.*, 1975, 586–599.

Hyrup et al., "Modification of the Binding Affinity of Peptide Nucleic Acids (PNA). PNA with Extended Backbones Consisting of 2–Aminoethyl–β–alanine or 3–Aminopropylglycine Units", *J. Chem. Soc., Chem. Commun.*, 1993, 518–519.

Inouye et al., "Selective Coloration of Spiro Pyridopyrans for Guanosine Derivatives", *J. Am. Chem. Soc.*, 1992, 114(2), 778–780.

Lin et al., "Synthesis and Biological Activity of Several Amino Analogues of Thymidine", *J. Med. Chem.*, 1978, 21(1), 109–112.

(List continued on next page.)

Primary Examiner—Robert A. Schwartzman
Assistant Examiner—M Schmidt
(74) Attorney, Agent, or Firm—Woodcock Washburn Kurtz Mackiewicz & Norris LLP

(57) ABSTRACT

Novel compounds that mimic and/or modulate the activity of wild-type nucleic acids. In general, the compounds contain a selected sequence of nucleosidic bases or other reactive groups that are covalently bound through nitrogen-containing linear, hairpin, dumbbell, and circular shaped tethers.

1 Claim, 9 Drawing Sheets

OTHER PUBLICATIONS

Loke et al., "Delivery of c–myc Antisense Phosphorothioate Oligodeoxynucleotides to Hematopoietic Cells in Culture by Liposome Fusion: Specific Reduction in c–myc Protein Expression Correlates with Inhibition of Cell Growth and DNA Synthesis", *Top. Microbiol. Immunol.*, 1988, 141, 282–289.

Ma et al., "Design and synthesis of RNA miniduplexes via a synthetic linker approach. 2. Generation of covalently closed, double–stranded cyclic HIV–1 TAR RNA analogs with high Tat–binding affinity", *Nucl. Acids. Res.*, 1993, 21(11), 2585–2589.

Marcus–Sekura et al., "Comparative inhibition of chloramphenicol acetyltransferase gene expression by antisense oligonucleotide analogues having alkyl phosphotriester, methylphosphonate and phosphorothiate linkages", *Nucl. Acids. Res.*, 1987, 15(14), 5749–5763.

Matteucci, "Deoxyoligonucleotide Analogs Based on Formacetal Linkages", *Tetra. Lett.*, 1990, 31(17), 2385–2388.

Mazur et al., "Isosteres of Natural Phosphates. 11. Synthesis of a Phosphonic Acid Analogue of an Oligonucleotide", *Tetrahedron*, 1984, 40(20), 3949–3956.

Miller et al., "Effects of a Trinucleotide Ethyl Phosphotriester, G'''p(Et)G'''p(Et)U, on Mammalian Cells in Culture", *Biochem.*, 1977, 16(9), 1988–1996.

Nair et al., "Regiospecific 5'-Silylation of Nucleosides", *Organic Prep. Proc. Int.*, 1990, 22(1), 57–61.

Nielsen et al., "Sequence–Selective Recognition of DNA by Strand Displacement with a Thymine–Substituted Polyamide", *Science*, 1991, 254, 1497–1500.

Niitsu et al., "Syntheses of a Series of Linear Pentaamines with Three and Four Methylene Chain Intervals", *Chem. Pharm. Bull.*, 1986, 34, 1032–1038.

Pauling, "Molecular Architecture and Biological Reactions", *Chem. Engin. News*, 1946, 24(10), 1375–1377.

Perkins et al., "Accelerated Displacement of Duplex DNA Strands by a Synthetic Circular Oligodeoxynucleotide", *J. Chem. Soc., Chem. Commun.*, 1993, 215–216.

Pitha, "Physiological Activities of Synthetic Analogs of Polynucleotides", *Adv. in Polymer Sci.*, 1983, 50, 2–16.

Prakash et al., "Molecular Recognition by Circular Oligonucleotides. Strong Binding of Single–stranded DNA and RNA", *J. Chem. Soc., Chem. Commun.*, 1991, 1161–1163.

Rebek, "Molecular Recognition and Biophysical Organic Chemistry", *Acc. of Chem. Res.*, 1990, 23(12), 399–404.

Rentzeperis et al., "Contribution of Loops and Nicks to the Formation of DNA Dumbbells: Melting Behavior and Ligand Binding", *Biochem.*, 1993, 32(10), 2564–2571.

Trapani et al., "N–1–Alkenyl–N,S–Diacyl–2–Aminobenzenethiols (Enamides) by Ring–Opening of 2,3–Dihydro–1,3–benzothiazoles with Aliphatic Carboxylic Anhydrides", *Synthesis*, 1988, 84–87.

Trost, B.M. and Fleming, I. (Eds.), *Comprehensive Organic Synthesis*, Pergamon Press, Oxford, 1991, 4, 758–776.

Tuladhar et al., "A Synthetic Route to Poly–N,N'–Dimethylethylenediamines", *Tetra. Lett.*, 1992, 33(16), 2203–2206.

Wilson, "Cellular Transport Mechanisms", *Ann. Rev. Biochem.*, 1978, 47, 933–965.

Wolfe, S. et al., "Five–Membered Rings. I. Inter and Intramolecular Reactions of Simple Amines with N–Substituted Phthalimides. Methylamine as a Reagent for Removal of a Phthaloyl Group from Nitrogen", *Canadian J. Chem.*, 1970, 48, 3572–3579.

Yamamoto et al., "One–step Synthesis of 5'Azido–nucleosides", *J. Chem. Soc. Perkin I*, 1980, 306–310.

Zuckermann et al., "Efficient Method for the Preparation of Peptoids [Oligo(N–substituted glycines)] by Submonomer Solid–Phase Synthesis", *J. Am. Chem. Soc.*, 1992, 114, 10646–10647.

Erwin et al., *Biochem. J.*, 1986, 238, 581–587.

Hyrup et al., *J. Am. Chem. Soc.*, 1994, 116, 7964–7970.

Kang et al., *Biopolymers*, 1992, 32(10), 1351–1363 (abstract).

McGraw et al., *Biotechniques*, 1990, 8(6), 674–678.

Morrison, R. and Boyd, R., *Organic Chemistry*, 3rd Ed., Boston, Allyn and Bacon, Inc., 1974, 738–740.

Westermann et al., *Biomed. Biochim Acta*, 1989, 48(1), 85–93.

Uhlmann et al., "Antisense Oligonucleotides: A New Therapeutic Principle", *Chem. Rev.*, 1990, 90(4), 543–584.

Miller, P.S., "Non–ionic Antisens Oligonucleotides", *Oligodeoxynucleotides*, 1989, Cohen, J.S. ed., CRC Press, Boca Raton, 79–95.

Goodchild, J., "Inhibition of Gene Expression by Oligonucleotides", *Oligodeoxynucleotides*, 1989, CRC Press, Boca Raton, 53–77.

Sereny, B., "Breakdown of Amino Acids by Enterobacteriaceae", *Acta Microbiol. Acad. Sci. Hung.*, 1966, 13, 167–169.

37

46
--- REPRESENTS WATSON-CRICK HYDROGEN BONDING

OLIGONUCLEOTIDE MIMICS HAVING NITROGEN-CONTAINING LINKAGES

This application is a continuation of U.S. application Ser. No. 08/180,124, filed Jan. 11, 1994, now U.S. Pat. No. 5,783,862, which is a continuation-in-part of the following U.S. applications: Ser. No. 08/039,979, filed Mar. 30, 1993, now abandoned; Ser. No. 08/039,846, filed Mar. 30, 1993 now abandoned; Ser. No. 08/040,933, filed Mar. 31, 1993, now abandoned; Ser. No. 08/040,903, filed Mar. 31, 1993, now U.S. Pat. No. 5,386,023; and Ser. No. 08/040,526, filed Mar. 31, 1993, now U.S. Pat. No. 5,489,677. Each of the foregoing are continuations-in-part of PCT/US92/04294, filed May 21, 1992, and of U.S. Ser. No. 07/903,160, filed Jun. 24, 1992, now abandoned, which are continuations-in-part of U.S. Ser. No. 07/703,619, filed May 21, 1991, now U.S. Pat. No. 5,378,825, which is a continuation-in-part of U.S. Ser. No. 07/566,836, filed Aug. 13, 1990, now U.S. Pat. No. 5,223,618, and U.S. Ser. No. 07/558,663, filed Jul. 27, 1990, now U.S. Pat. No. 5,138,045. Each of these patent applications are assigned to the assignee of this application and are incorporated by reference herein.

FIELD OF THE INVENTION

This invention relates to the design, synthesis and application of oligonucleotide mimics. More particularly, the invention relates to linear, duplex, hair-pin, stem-loop and cyclic compounds wherein naturally-occurring nucleobases, nucleobase-binding moieties, or other chemically active moieties are covalently bound to a somewhat linear, heteroatom-containing backbone.

BACKGROUND OF THE INVENTION

It is well known that most of the bodily states in mammals, including most disease states, are effected by proteins. Proteins, either acting directly or through their enzymatic functions, contribute in major proportion to many diseases in animals and man.

Classical therapeutics generally has focused upon interactions with proteins in an effort to moderate their disease causing or disease potentiating functions. Recently, however, attempts have been made to moderate the production of proteins by interactions with the molecules (i.e., intracellular RNA) that direct their synthesis. These interactions have involved hybridization of complementary "antisense" oligonucleotides or certain analogs thereof to RNA. Hybridization is the sequence-specific hydrogen bonding of oligonucleotides or oligonucleotide analogs to RNA or to single stranded DNA. By interfering with the production of proteins, it has been hoped to effect therapeutic results with maximum effect and minimal side effects.

The pharmacological activity of antisense oligonucleotides and oligonucleotide analogs, like other therapeutics, depends on a number of factors that influence the effective concentration of these agents at specific intracellular targets. One important factor for oligonucleotides is the stability of the species in the presence of nucleases. It is unlikely that unmodified oligonucleotides will be useful therapeutic agents because they are rapidly degraded by nucleases. Modification of oligonucleotides to render them resistant to nucleases therefore is greatly desired.

Modification of oligonucleotides to enhance nuclease resistance generally has taken place on the phosphorus atom of the sugar-phosphate backbone. Phosphorothioates, methyl phosphonates, phosphoramidates and phosphorotriesters have been reported to confer various levels of nuclease resistance. Phosphate-modified oligonucleotides, however, generally have suffered from inferior hybridization properties. See, e.g., Crooke, S. T. and Lebleu, B., eds., *Antisense Research and Applications* (CRC Press, Inc., Boca Raton Fla., 1993).

Another key factor is the ability of antisense compounds to traverse the plasma membrane of specific cells involved in the disease process. Cellular membranes consist of lipid-protein bilayers that are freely permeable to small, nonionic, lipophilic compounds and are inherently impermeable to most natural metabolites and therapeutic agents. See, e.g., Wilson, *Ann. Rev. Biochem.* 1978, 47, 933. The biological and antiviral effects of natural and modified oligonucleotides in cultured mammalian cells have been well documented. It appears that these agents can penetrate membranes to reach their intracellular targets. Uptake of antisense compounds into a variety of mammalian cells, including HL-60, Syrian Hamster fibroblast, U937, L929, CV-1 and ATH8 cells has been studied using natural oligonucleotides and certain nuclease resistant analogs, such as alkyl triesters and methyl phosphonates. See, e.g., Miller, et al., *Biochemistry* 1977, 16, 1988; Marcus-Sekura, et al., *Nuc. Acids Res.* 1987, 15, 5749; and Loke, et al., *Top. Microbiol. Immunol.* 1988, 141, 282.

Often, modified oligonucleotides and oligonucleotide analogs are internalized less readily than their natural counterparts. As a result, the activity of many previously available antisense oligonucleotides has not been sufficient for practical therapeutic, research or diagnostic purposes. Two other serious deficiencies of prior art compounds designed for antisense therapeutics are inferior hybridization to intracellular RNA and the lack of a defined chemical or enzyme-mediated event to terminate essential RNA functions.

Modifications to enhance the effectiveness of the antisense oligonucleotides and overcome these problems have taken many forms. These modifications include base ring modifications, sugar moiety modifications and sugar-phosphate backbone modifications. Prior sugar-phosphate backbone modifications, particularly on the phosphorus atom, have effected various levels of resistance to nucleases. However, while the ability of an antisense oligonucleotide to bind to specific DNA or RNA with fidelity is fundamental to antisense methodology, modified phosphorus oligonucleotides have generally suffered from inferior hybridization properties.

Replacement of the phosphorus atom has been an alternative approach in attempting to avoid the problems associated with modification on the pro-chiral phosphate moiety. For example, Matteucci, *Tetrahedron Letters* 1990, 31, 2385 disclosed the replacement of the phosphorus atom with a methylene group. However, this replacement yielded low affinity compounds with nonuniform insertion of formacetal linkages throughout their backbones. Cormier, et al., *Nucleic Acids Research* 1988, 16, 4583, disclosed replacement of phosphorus with a diisopropylsilyl moiety to yield homopolymers having poor solubility and hybridization properties. Stirchak, et al., *Journal of Organic Chemistry* 1987, 52, 4202, disclosed that replacement of phosphorus linkages by short homopolymers containing carbamate or morpholino linkages to yield compounds having poor solubility and hybridization properties. Mazur, et al., *Tetrahedron* 1984, 40, 3949, disclosed replacement of a phosphorus linkage with a phosphonic linkage yielded only a homotrimer molecule. Goodchild, *Bioconjugate Chemistry* 1990, 1, 165, disclosed ester linkages that are enzymatically degraded by esterases and, therefore, are not suitable for antisense applications.

The limitations of available methods for modification of the phosphorus backbone have led to a continuing and long felt need for other modifications which provide resistance to nucleases and satisfactory hybridization properties for antisense oligonucleotide diagnostics and therapeutics.

Consequently, there is considerable interest in developing oligonucleotide surrogates that are capable of maintaining Watson-Crick base pairing to native RNA (DNA) or duplex DNA targets (formation of a triplex) but do not contain the usual phosphodiester linkages. One of the approaches to this problem involves the use of backbones containing peptide type linkages which connect the bases required for base pairing. These compounds are commonly known as peptide nucleic acids (PNA). Thus, in principle, it should be possible to design reagents or molecules that recognize any predetermined sequence, simply by connecting nucleosidic bases or other ligands with appropriate linear spacer molecules to maintain a desired geometry required for recognition of the hydrogen bonding groups in the minor or major groove of a nucleic acid. Recently, PNA and related molecules have demonstrated high affinity and specificity towards nucleic acid targets (Egholm, et. al., *J. Am. Chem. Soc.* 1992, 114, 1895, 9667; Nielsen, et. al., *Science* 1991, 254, 1497; Hyrup, et. al., *J. Chem. Soc. Chem. Comm.* 1993, 518).

Molecular recognition plays a key role in the binding step, that is, the formation of the stable reactive complex. Much work has been done on the so called molecular clefts, where molecules are constructed so that they can recognize specific nucleobases by base pairing or base stacking (Rebek, Jr. *Acc. Chem. Res.* 1990, 23, 399; Inouye, et. al., *J. Am. Chem. Soc.* 1992, 114, 778.) It is believed that convergent functionality would provide an advantage in that activity could be 'focused' in a highly localized manner at an active site. The ultimate goal is to merge the recognition and reaction steps in space and in time such that maximum binding would occur to transition states, as was anticipated by Pauling, *Chem. Eng. News* 1946, 24, 1375.

There remains a need in the art for molecules which have fixed preorganized geometry that matches that of a target such as a nucleic acid or protein. The backbone of such molecules should be rigid with some flexibility and easy to construct in solution or via automated synthesis on solid support.

OBJECTS OF THE INVENTION

It is an object of the invention to provide oligonucleotide mimics for diagnostic, research, and therapeutic use.

It is a further object of the invention to provide oligonucleotide mimics capable of forming duplex or triplex structures with, for example, DNA.

It is a further object to provide oligonucleotide mimics having enhanced cellular uptake.

Another object of the invention is to provide oligonucleotide mimics having greater efficacy than unmodified antisense oligonucleotides.

It is yet another object of the invention to provide methods for synthesis of linear, hairpin, dumbbell or circular molecules as oligonucleotide mimics.

These and other objects will become apparent to persons of ordinary skill in the art from a review of the present specification and the appended claims.

SUMMARY OF THE INVENTION

The present invention provides novel compounds that mimic and/or modulate the activity of wild-type nucleic acids and proteins. In certain embodiments, the compounds contain a selected nucleobase sequence which is hybridizable with a targeted nucleoside sequence of single stranded or double stranded DNA or RNA. At least a portion of the compounds of the invention has structure I:

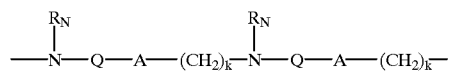

wherein:

each $R_N$ is, independently, H, —T—L, alkyl having 1 to about 10 carbon atoms; alkenyl having 2 to about 10 carbon atoms; alkynyl having 2 to about 10 carbon atoms; aryl having 7 to about 14 carbon atoms; heterocyclic; a reporter molecule; an RNA cleaving group; a group for improving the pharmacokinetic properties of the compound; or a group for improving the pharmacodynamic properties of the compound;

each Q is, independently, N—$R_N$, O, S, SO, $SO_2$, or $CH_2$;

k is zero or 1;

each A is, independently, $R_S$—X(T—L)—$R_S$; N—$R_N$; C(O); a single bond; or $(CH_2)_m$ where m is 1–5;

each $R_S$ is, independently, a single bond or alkyl having 1 to about 12 carbon atoms;

each T is, independently, a single bond, a methylene group or a group having structure II:

—[$CR^1R^2$]$_n$—B—[$CR_1R_2$]$_o$—[D]$_p$—[N($R_N$)]$_q$—  II where:

D is C(O), C(S), C(Se), $C(R^1)(NR^3R^4)$, $CH_2R^1$, $CHR^1R^2$, or $NR^3R^4$;

B is a single bond, CH=CH, C≡C, O, S or $NR^4$;

each $R^1$ and $R^2$ is independently selected from the group consisting of hydrogen, alkyl or alkenyl having 1 to about 12 carbon atoms, hydroxy- or alkoxy- or alkylthio-substituted alkyl or alkenyl having 1 to about 12 carbon atoms, hydroxy, alkoxy, alkylthio, amino and halogen;

$R^3$ and $R^4$, independently, are H, —T—L, alkyl having 1 to about 10 carbon atoms; alkenyl having 2 to about 10 carbon atoms; alkynyl having 2 to about 10 carbon atoms; aryl having 7 to about 14 carbon atoms; heterocyclic; a reporter molecule; an RNA cleaving group; a group for improving the pharmacokinetic properties of the compound; or a group for improving the pharmacodynamic properties of the compound; or $R^3$ and $R^4$, together, are cycloalkyl having 3 to about 10 carbon atoms or cycloalkenyl having 4 to about 10 carbon atoms;

n and o, independently, are zero to 5;

q is zero or 1;

p is zero to about 10;

each L is, independently, a nucleosidic base, an amino acid side chain, an aromatic hydrocarbon, a heterocycle moiety containing nitrogen, sulfur, and/or oxygen; a carbohydrate, a drug, a reporter molecule; an RNA cleaving group; a group for improving the pharmacokinetic properties of the compound; or a group for improving the pharmacodynamic properties of the compound; or group capable of hydrogen bonding;

each X is, independently, N or CH, or X and T, together, form an aromatic moiety, a pentose, a hexose, or a deoxy derivative of a pentose or a hexose.

The compounds of the invention generally are prepared by coupling preselected bifunctional synthons under conditions effective to form the above-noted structures. In certain embodiments, the compounds of the invention are prepared by intermolecular reductive coupling of, for example, a hydrazine moiety on a first synthon with an aldehyde moiety on a second synthon. In other embodiments, the compounds of the invention are prepared by coupling a carbocentric radical on a first synthon with, for example, a radical acceptor moiety on a second synthon. In further embodiments, the compounds are prepared through a nucleophilic alkylation wherein a nucleophilic moiety on a first synthon displaces a leaving group on a second synthon.

BRIEF DESCRIPTION OF THE DRAWINGS

The numerous objects and advantages of the present invention may be better understood by those skilled in the art by reference to the accompanying figures, in which.

DETAILED DESCRIPTION OF THE INVENTION

Figure 1:
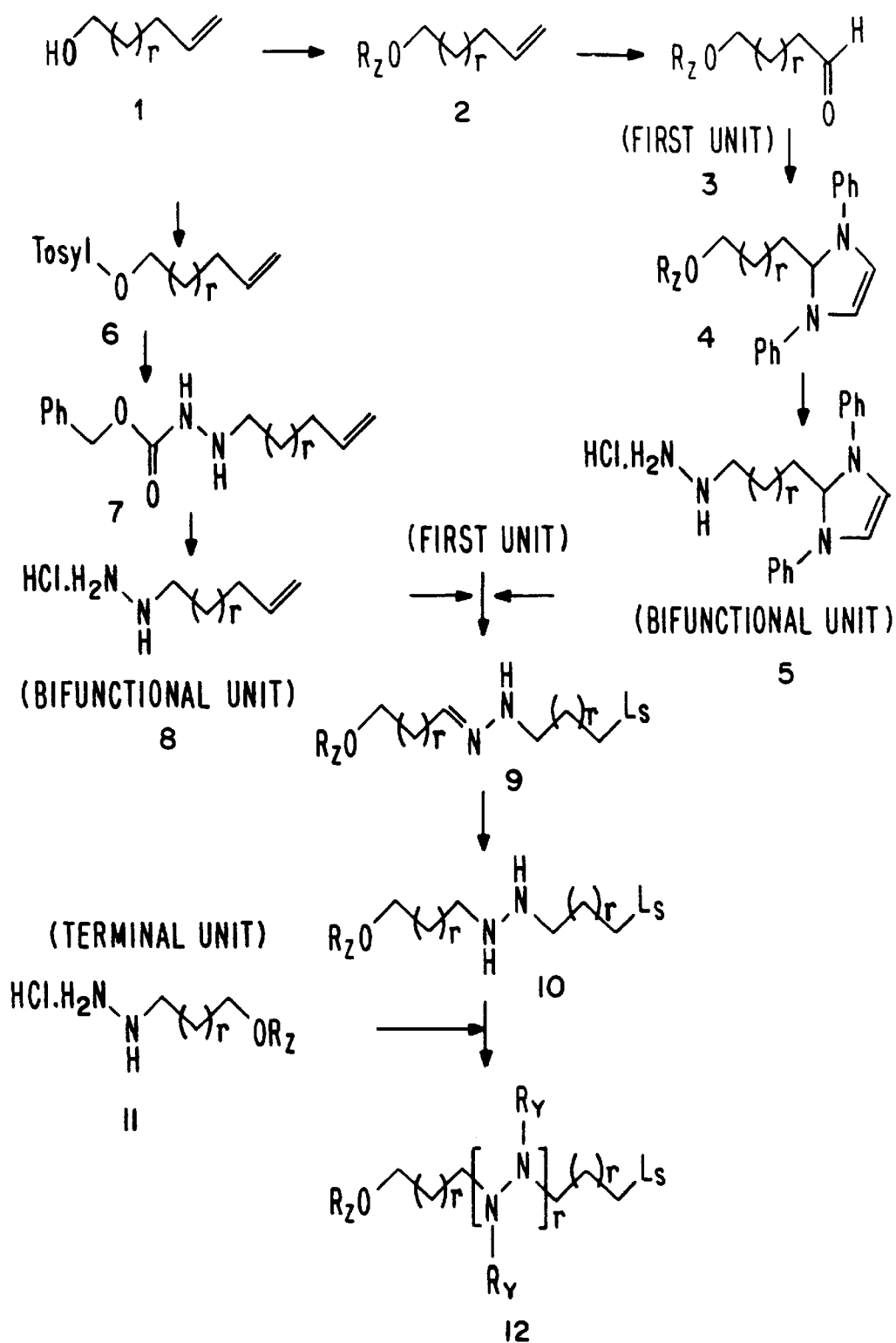
FIG. 1 shows solid phase and solution phase processes for synthesis of hydrazino-linked compounds according to the invention.

In designing novel drugs that recognize specific DNA sequences or protein binding sites, it is important to have thermodynamic information on the structure of the complexes. In particular, single stranded hairpin-shaped or dumbbell-shaped molecules are favorable for these studies because they form stable duplexes of defined geometry and secondary structure (see, e.g., Ma, et. al., *Nucleic Acids Research* 1993, 21, 2585; Rentzeperis, et. al., *Biochemistry* 1993, 32, 2564.) The structure and overall physical properties of such preorganized oligomeric molecules may be useful both to study nucleic acid-protein interactions as well as to provide a means for therapeutic inventions as transcription decoys.

In addition, methods are available to further stabilize the secondary structure of synthetic molecules by crosslinking without perturbing their native geometries. (see, e.g., PCT/US93/02059, filed Mar. 5, 1993 and incorporated herein by reference). We would like to utilize the chemistries described herein to trap, isolate, and even circularize the oligomer under the given conditions. Thus, it should be possible to target single strands of nucleic acids (e.g., m-RNA) using circular oligomers. (see, e.g., Perkin, et. al., *J. Chem. Soc. Chem. Comm.* 1993, 215).

The term "nucleoside" as used in connection with this invention refers to a unit made up of a heterocyclic base and a sugar. The term "nucleotide" refers to a nucleoside having a phosphate group on its 3' or 5' sugar hydroxyl group. Thus nucleosides, unlike nucleotides, have no phosphate group. "Oligonucleotide" refers to a plurality of joined nucleotide units formed in a specific sequence from naturally occurring bases and pentofuranosyl groups joined through a sugar group by native phosphodiester bonds. This term refers to both naturally occurring and synthetic species formed from naturally occurring subunits.

The compounds of the invention generally can be viewed as "oligonucleotide mimics", that is, compounds which function like oligonucleotides but which have non-naturally occurring portions. Oligonucleotide mimics can have altered sugar moieties or no sugar moieties, altered base moieties or altered inter-sugar linkages. Representative modified bases include deaza or aza purines and pyrimidines used in place of natural purine and pyrimidine bases; pyrimidines having substituent groups at the 5 or 6 position; purines having altered or replacement substituent groups at the 2, 6 or 8 positions. Representative modified sugars include carbocyclic or acyclic sugars, sugars having substituent groups at their 2' position, and sugars having substituents in place of one or more hydrogen atoms of the sugar. Other altered base moieties and altered sugar moieties are disclosed in U.S. Pat. No. 3,687,808 and PCT application PCT/US89/02323.

Altered base moieties or altered sugar moieties also include other modifications consistent with the spirit of this invention. Such compounds are best described as moieties that are structurally distinguishable from yet functionally interchangeable with naturally occurring or synthetic wild type oligonucleotides. All such compounds are comprehended by this invention so long as they function effectively to mimic the structure of a desired RNA or DNA strand.

For use in antisense methodology, the oligonucleotide mimics of the invention preferably comprise from about 10 to about 30 bases. It is more preferred that such mimics comprise from about 15 to about 25 bases.

It is preferred that the RNA or DNA portion which is to be modulated using oligonucleotide mimics of the invention be preselected to comprise that portion of DNA or RNA which codes for the protein whose formation or activity is to be modulated. The targeting portion of the composition to be employed is, thus, selected to be complementary to the preselected portion of DNA or RNA, that is, to be an antisense oligonucleotide mimic for that portion.

In accordance with one preferred embodiment of this invention, the compounds of the invention hybridize to HIV mRNA encoding the tat protein or to the TAR region of HIV mRNA. In another preferred embodiment, the compounds mimic the secondary structure of the TAR region of HIV mRNA and by doing so bind the tat protein. Other preferred compounds are complementary to sequences for herpes, papilloma and other viruses.

The oligonucleotide mimics of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be treated with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, since each cell of multicellular eukaryotes can be treated since they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotide mimics. As used herein, therapeutics is meant to include the eradication of a disease state, by killing an organism or by control of erratic or harmful cellular growth or expression.

The oligonucleotide mimics of the invention are believed to exhibit increased stability relative to their naturally occurring counterparts. Extracellular and intracellular nucleases generally do not recognize—and therefore do not degrade—the compounds of the invention. In addition, the neutral or positively charged compounds of the present invention can be taken into cells by simple passive transport rather than by complex, protein-mediated processes. Another advantage of the invention is that the absence of a negatively charged backbone facilitates sequence specific binding of the oligonucleotide mimics to targeted RNA, which has a negatively charged backbone and will repel similarly charged oligonucleotides. Still another advantage of the present invention is that it presents sites for attaching functional groups that initiate cleavage of targeted RNA.

The term heterocyclic is intended to denote moieties wherein a heteroatoms is inserted into the carbon backbone of an aromatic or alicyclic moiety. Representative heteroatoms include N, O, S, Se, and Te. The terms alkyl, aryl, alkenyl, and alkynyl are intended to include straight-chain, branched, and cyclic moieties, including those substituted with, for example, hydroxyl, alkoxy, alcohol, benzyl, phenyl, nitro, thiol, halogen, or alkyl, aryl, alkenyl, or alkynyl groups. Groups that enhance pharmacodynamic properties improve oligonucleotide uptake, enhance oligonucleotide resistance to degradation, and/or strengthen sequence-specific hybridization with RNA. Groups that enhance pharmacokinetic properties improve oligonucleotide transport, uptake, distribution, metabolism or excretion.

The compounds of the invention generally are prepared by coupling preselected bifunctional synthons under conditions effective to form compounds having structure I. In certain embodiments, the compounds of the invention are prepared by intermolecular reductive coupling. In other embodiments, the compounds of the invention are prepared by intermolecular radical addition reactions. In further embodiments, the compounds are prepared by nucleophilic displacement. In each of these embodiments, free amino groups in the resulting linkage can be further functionalized. For example, the nucleophilic amino group can be reacted with a group having structure $R_L$—T—L, thereby displacing the $R_L$ leaving group and forming a covalent —N—T—T, linkage.

In the reductive coupling methods, compounds having structure I are formed by coupling synthons having structures III and IV:

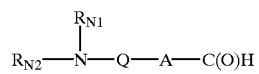

III

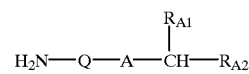

IV wherein:

$R_{N1}$ and $R_{N2}$ are, independently, amine protecting groups, or a group comprising: [N ($R_N$)—Q—A—CH$_2$]$_r$, where r is 1–100, a nucleoside, a nucleotide, an oligonucleotide, an oligonucleotide analog, an oligonucleoside, a PNA or a hydroxyl-protected and/or amine-protected derivative thereof, or $R_{N1}$ and $R_{N2}$, together, form an amine protecting group; and $R_{A1}$ and $R_{A2}$ are, independently, carbonyl protecting groups, or a group comprising: [N ($R_N$)—Q—A—CH$_2$]$_r$, where r is 1–100, a nucleoside, a nucleotide, an oligonucleotide, an oligonucleotide analog, an oligonucleoside, a PNA or a hydroxyl-protected and/or amine-protected derivative thereof, or $R_{A1}$ and $R_{A2}$, together, form a carbonyl protecting group.

The radical addition reactions can be divided into two steps. The first step involves generation of an initial radical, which undergoes the desired reaction. The second step involves removal of the radical from the reaction before the occurrence of an intervening, undesired reaction such as cross coupling. In certain embodiments, the compounds of the invention are prepared by providing a donor synthon having structure V and an acceptor synthon having structure VI where $R_B$ is a radical generating group, generating a carbocentric radical at the —CH$_2$—$R_B$ position, and then forming an intermolecular linkage by reacting radical-bearing donor synthon V with acceptor synthon VI. Radical generating groups according to the invention include I, OC(S)O—C$_6$H$_5$, Se—C$_6$H$_5$, OC(S)O—C$_6$F$_5$, OC(S)O—C$_6$Cl$_5$, OC(S)O—(2,4,6—C$_6$Cl$_3$), Br, NO$_2$, Cl, OC(S)S—Me, OC(S)O—(p—CH$_4$F), bis-dimethylglyoximato-pyridine cobalt, OC(S)C$_6$H$_5$, OC(S)SCH$_3$, OC(S)-imidazole, and OC(O)O-pyridin-2-thione.

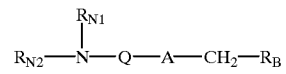

V

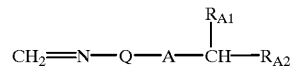

VI

The nucleophilic displacement (alkylation) reactions involve reacting a first synthon VII bearing a leaving group, $R_L$, with a second synthon VIII bearing a nucleophilic nitrogen moiety under conditions effective to displace the leaving group and form the above-identified linkages.

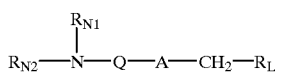

VII

-continued

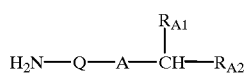

VIII

Leaving groups according to the invention include chloro, fluoro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl groups.

Reductive Coupling

The linkages of the invention can be formed by selecting a formyl-derivatized compound (e.g., structure III) as an upstream synthon and an amino-derivatized compound (e.g., structure IV) as a downstream synthon.

Formyl-terminated compounds such as structure III can be formed via several synthetic pathways. One preferred method utilizes a radical reaction of the corresponding xanthate-terminated compound. The xanthate compound is treated with 2,2'-azobisisobutrylonitrile (AIBN), and tributyltin styrene in toluene. Subsequently, the styrene derivative is hydroxylated and cleaved to furnish a formyl group. Alternately, formyl-terminated compounds can be synthesized from a cyano-terminated compound by techniques well known in the art. Terminal formyl groups can be blocked in a facile manner, for example, utilizing o-methylaminobenzenthiol as a blocking group. The formyl blocking group can be deblocked with silver nitrate oxidation.

An alternate method of preparing formyl-terminated compounds employs tosylation of a terminal hydroxyl group, which on iodination followed by cyanation with KCN in DMSO will furnish a nitrile. Reduction with DIBAL-H gives the desired formyl-terminated compound. In yet another method, a terminal C=C bond is oxidized with $OsO_4$ and cleavage of the resulting diol with $NaIO_4$ gives the desired formyl functionality.

Hydroxylamino terminated compounds such as those having structure IV (Q=O) can be prepared by treating the corresponding hydroxyl compound with N-hydroxyphthalimide, triphenylphosphine and diethylazodicarboxylate under Mitsunobu conditions to provide an O-phthalimido derivative. The free hydroxylamino compound can be generated in quantitative yield by hydrazinolysis of the O-phthalimido derivative.

Hydrazino-terminated compounds such as those having structure IV (Q=NH) can be prepared by treating hydroxyl-terminated compounds with tosyl chloride in pyridine to give an O-tosylate derivative. Treatment of benzylcabazide with O-tosylate will furnish a benzylcarbazide derivative, which on hydrogenation provides the free hydrazino moiety for reductive coupling.

Amino-terminated compounds such as those having structure IV (Q=$CH_2$) can be synthesized by treating the corresponding hydroxyl-terminated compound with $Ph_3P$, $CBr_4$ and $LiN_3$ according to the procedure of Hata, et al., *J. Chem. Soc. Perkin* 1 1980, 306, to furnish a terminal azide. Reduction of the azido group with tributyltin hydride provides the desired amino functionality.

Coupling of structures III and IV then is effected to furnish a dimeric unit having an imine or oxime linkage. This linkage then is reduced in situ with $NaCNBH_3$ to furnish a —C—N— linked unit. In certain embodiments these —C—N— linked units contain two hydroxyl groups, one placed at the upstream end and the other placed at downstream end. One of these groups can be protected with a dimethoxytrityl group, and the other group can be protected as a cyanoethyldiisopropyl-phosphite. These units can be inserted into any desired sequence by standard, solid phase, automated DNA synthesis utilizing standard phosphoramidite chemistry. (see, e.g., Protocols For Oligonucleotides And Analogs, Agrawal, S., ed., Humana Press, Totowa, N.J., 1993.)

Thus, one or more of such oligomeric units can be attached, as in Example 1, at the ends of a DNA sequence or placed internally connected by phosphodiester linkages. The resulting oligonucleotide analog or oligomer has a "mixed" backbone containing more than one type of linkages of this invention. In a similar manner, an oligomer containing alternating phosphodiester linkages can be prepared. Such a structure should provide enhanced affinity and base-pair specificity towards the nucleic acid targets and proteins. Furthermore, these structures should have increased hydrophilicity compared to an oligomer without phosphate linkages.

Oligomers containing a uniform backbone linkage can be synthesized using CPG-solid support and standard nucleic acid synthesizing machines such as Applied Biosystems Inc. 380B and 394 and Milligen/Biosearch 7500 and 8800s. The initial monomer (number 1 at the 3'-terminus) is attached, via an appropriate linker, to a solid support such as controlled pore glass or polystyrene beads. In sequence specific order, each new monomer (e.g., structure III or IV) is attached either by manual manipulation or by the automated synthesizer system. In the case of a methylenehydrazine linkage (Q=N), the repeating nucleoside unit can be of two general types: a linear structure with a protected aldehydic function at one end and a C-hydrazinomethyl group at the opposite end, or a structure bearing a terminal hydrazino group and a protected C-formyl group. In each case, the conditions that are repeated for each cycle to add the subsequent base include: acid washing to remove the terminal aldehydo protecting group; addition of the next molecule with a methylenehydrazino group to form the respective hydrazone connection; and reduction with any of a variety of agents to afford the desired methylene-hydrazine linked CPG- or polystyrene-bound structure. One such useful reducing agent is sodium cyanoborohydride.

A preferred method is shown in FIG. 1. This method utilizes a solid support to which a linear molecule having a protected aldehyde or an aldehyde precursor at its terminal end is attached. The terminal aldehyde can be suitably protected with various groups, such as described by Greene and Wuts in *Protective Groups in Organic Synthesis*, John Wiley & Sons, Inc., 1991, pp 175–223. In one preferred method, the aldehyde group is protected with N,N'-diphenyl imidazolidine, which can be cleaved with aqueous HCl as described by Giannis, et al. *Tetrahedron* 1988, 44, 7177. 2,3-Dihydro-1,3-benzo-thiazole is yet another preferred protecting group for aldehyde functionality and is cleaved by $AgNO_3$ at neutral pH (see, e.g., Trapani, et. al., *Synthesis* 1988, 84). More preferably, a terminal vinyl group is oxidized with $OsO_4$ and cleaved with $NaIO_4$ to yield a free aldehydo group.

A bifunctional synthon having a protected aldehydo group at one end (the masked coupling end) and a hydrazino group at the opposite end (the reactive coupling end) can be coupled under acidic conditions with a linear aldehyde attached to the solid support. The intermediate hydrazone then is reduced with NaBH$_3$CN to furnish a hydrazino linkage attached to the solid support.

Subsequently, bisalkylation of the hydrazino moiety via an appropriate halide or aldehyde provides a N,N-substituted hydrazine linked to the solid support. Thereafter, the cycle can be repeated by the addition of bifunctional synthon under acidic conditions, reduction, and alkylation of hydrazine moiety to create a polymeric molecule of a desired sequence connected by one or more substituted hydrazino linkages. In some preferred embodiments of this invention, the final unit utilized for coupling can bear a phosphate or a phosphonate linkage to provide water solubility for such molecules.

One preferred process employees an aldehyde-protected synthon attached to the solid support. Attachments can be effected via standard procedures as described by R. T. Pon in Protocols For Oligonucleotides And Analogs, Chapter 24, Agrawal, S., ed., Humana Press, Totowa, N.J., 1993.

As an alternative, a solution phase synthesis of substituted hydrazino linked linear molecules can be accomplished via hydroxyl protected synthons, such as shown in FIG. 1 (R$_Z$=hydroxyl protecting group or solid support) utilizing a t-butyl diphenylsilyl group.

Figure 4:
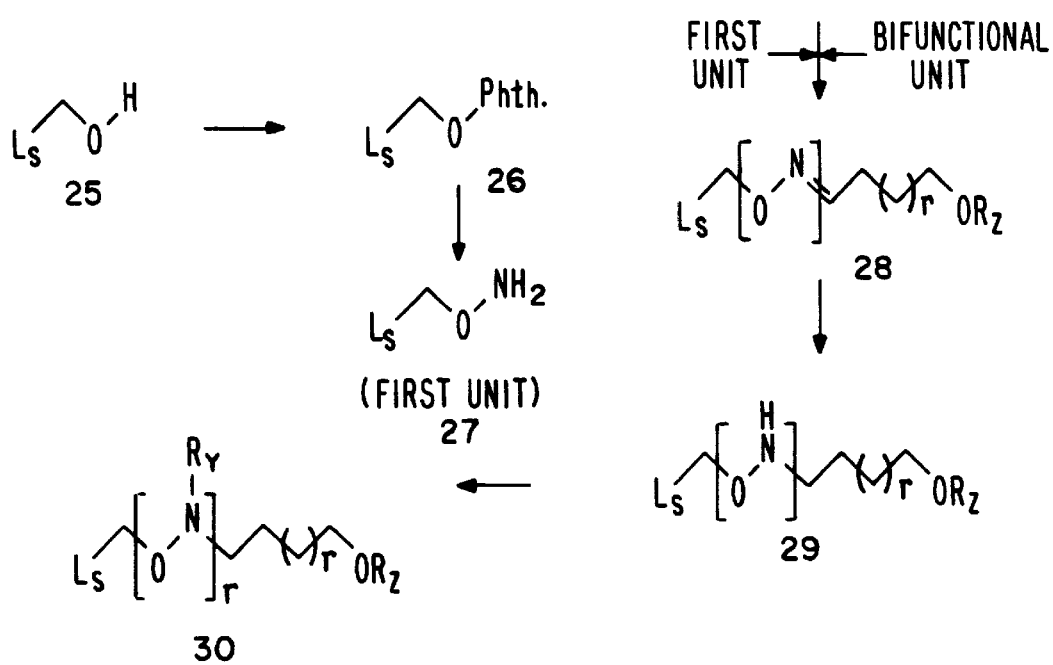
FIG. 4 shows solid phase and solution processes for synthesis of hydroxylamino-linked compounds according to the invention.

A further method of synthesizing N-substituted hydroxylamine linked linear molecules is depicted in FIG. 4 (L$_S$=a linker attached to solid support, or a protecting group, such as t-butyldiphenylsilyl). This method also employs a solid support to which a linear molecule having an O-phthalimido group at its terminal end is attached. A further bifunctional unit that has an aldehyde functionality at the coupling end and an O-phthalimido group at the growing end is utilized as the middle block via repeating cycles. The synthesis of polymeric structures can be stopped by use of a terminating unit that bears a hydroxyl protecting group rather than a phthalimido group. A wide variety of hydroxyl protecting groups can be employed in the methods of the invention. In general, protecting groups render chemical functionality inert to specific reaction conditions, and can be appended to and removed from such functionality in a molecule without substantially damaging the remainder of the molecule. Representative protecting groups are disclosed by Beaucage, et al., *Tetrahedron* 1992, 48, 2223.

The O-phthalimido group attached to the support is hydrazinolyzed with methyl-hydrazine to generate a reactive O-amino group. Acid catalyzed coupling of the resulting bifunctional unit provides an oxime linked support. The oxime linkage can be reduced with NaBH$_3$CN/acetic acid to yield a hydroxyl amino linkage, which is then alkylated with appropriate functionality. Alternately, the coupled unit can be treated with methyl hydrazine and the coupling with bifunctional unit repeated until an oligomer of desired length is obtained. The multiple oxime linkages thus created can be reduced in one step utilizing NaBH$_3$CN/AcOH to create free O-amino groups, which can be further substituted uniformly with appropriate functionality.

In a similar manner, a solution phase synthesis of such polymeric molecules connected via substituted hydroxylamino linkages utilizes the coupling/reduction/alkylation hydrazinolysis steps in a sequential order, starting with a hydroxyl protected molecule.

Radical Coupling

The radical-based methods of the invention generally involve "nonchain" processes. In nonchain processes, radicals are generated by stoichiometric bond homolysis and quenched by selective radical-radical coupling. It has been found that bis(trimethylstannyl)benzopinacolate and bis(tributylstannyl)benzopinacolate (see, e.g., *Comprehensive Organic Synthesis*: Ed. by B. M. Trost & J. Fleming, Vol. 4, pp 760)—persistent radicals—can be used to enhance the radical-radical coupling and reduce cross-coupling. It will be recognized that a persistent radical is one that does not react with itself at a diffusion-controlled rate. Hillgartner, et al., *Liebigs. Ann. Chem.* 1975, 586, disclosed that on thermolysis (about 80° C.) pinacolate undergoes homolytic cleavage to give the suspected persistent radical (Ph$_2$C*OSnMe$_3$), which stays in equilibrium with benzophenone and the trimethylstannyl radical (Me$_3$Sn*). It is believed that the Me$_3$Sn* radical abstracts iodine from radical precursors such as iodo-terminated compounds having structure V to give radical-terminated intermediates. The radicals then add to immino acceptors such as structure VI to yield a —C—C—N— linkage.

At high concentrations the initial radical can be trapped by coupling prior to addition, and at low concentrations the adduct radical can begin to telomerize. It is believed that a three molar equivalent excess of pinacolate provides satisfactory results for such couplings. The efficiency of radical reactions is highly dependent on the concentration of the reagents in an appropriate solvent. Preferably, the reaction mixture contains benzene, dichlorobenzene, t-butylbenzene, t-butyl alcohol, water, acetic acid, chloroform, dichloro methane, carbon tetrachloride, or mixtures thereof. The solvent should contain a combined concentration of about 0.1 to about 0.4 moles/liter of radical precursor and acceptor, preferably about 0.1 to about 0.2 moles/liter. It has been found that best results are obtained using benzene solutions containing about 0.2 moles/liter of radical precursor and acceptor.

Figure 5:
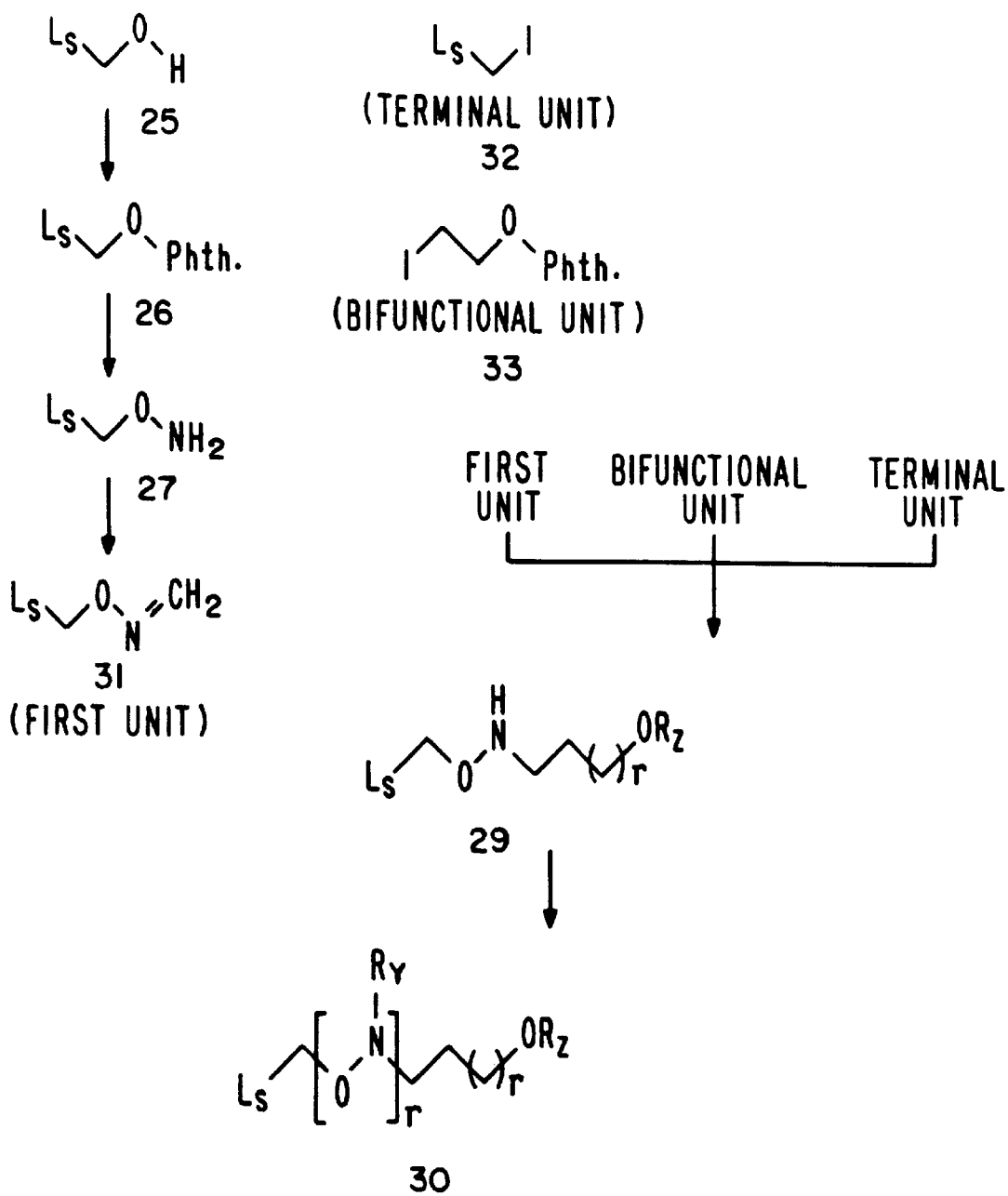
FIG. 5 shows a synthetic scheme for synthesis of hydroxylamino-linked compounds according to the invention by radical coupling methodology.
Figure 6A:
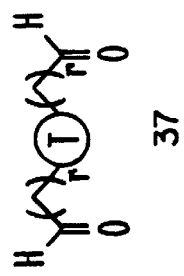
FIG. 6 shows solid phase processes for synthesis of duplex, hairpin, stem-loop, and cyclic hydroxylamino-linked compounds according to the invention.
Figure 6A:
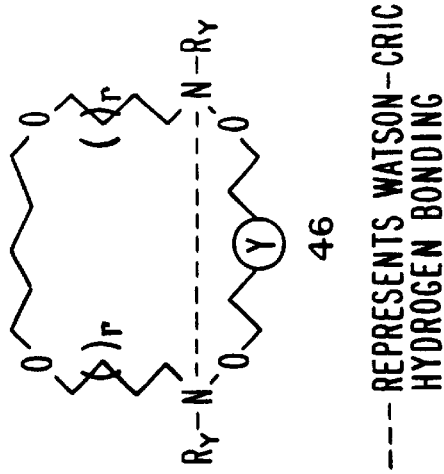
Figure 6A:
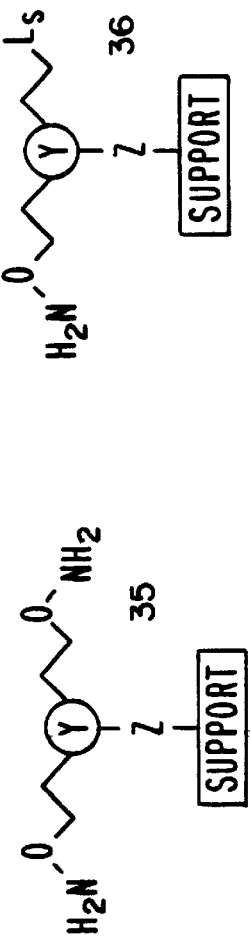
Figure 6A:
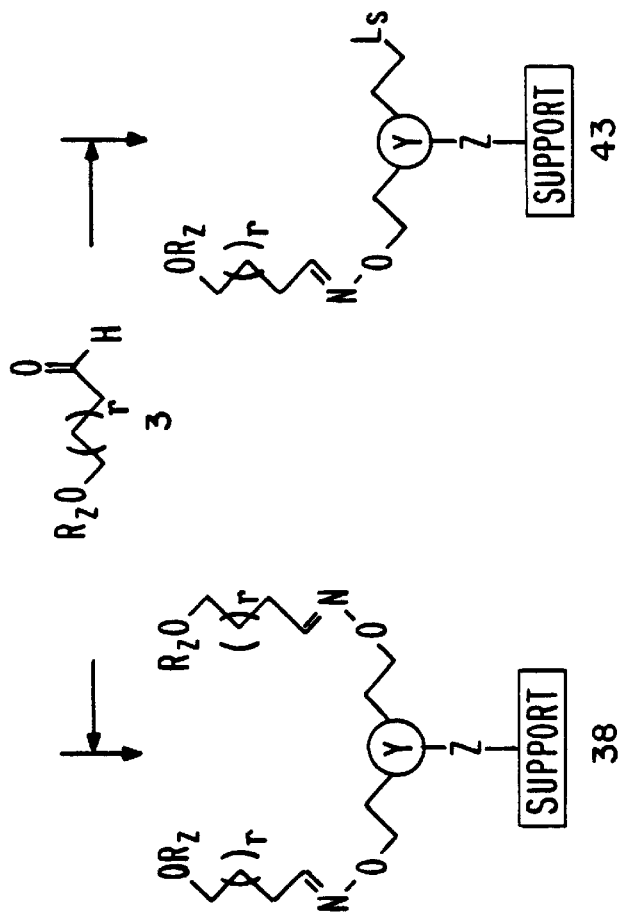
Figure 6B:
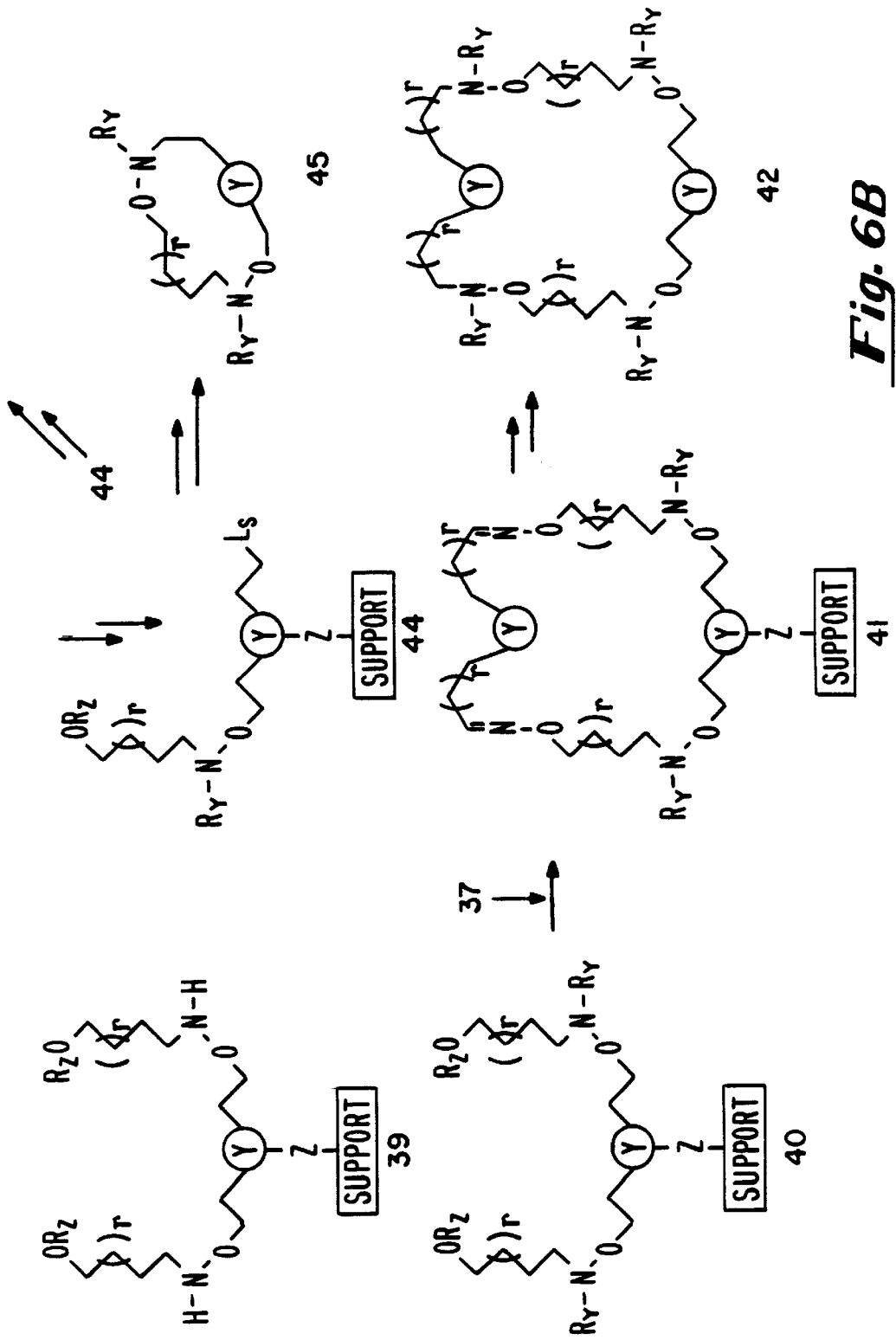

As exemplified in FIG. 5, the radical coupling of an oxime ether 31 as an acceptor with radical precursor 33 occurs in the presence of bis(trimethylstannyl)benzopinacolate in refluxing benzene. The reaction is carried out under argon and a 35–50% isolated yield of the product is obtained after purification. The hydroxylamino linkages thus obtained can be alkylated with an appropriate functionality. Subsequently, the hydroxyl group is deblocked and treated with N-hydroxyphthalimide under Mitsunobu conditions to yield an O-phthalimido derivative. Hydrazinolysis and formylation of the latter compound gives an oxime ether functionality at the reactive end of the molecule. Therefore, a radical coupling cycle can be repeated with high chemoselectivity to yield an oligomer or polymeric unit linked via one or more substituted hydroxylamino linkages. The chain elongation can be terminated at any point during the described method by avoiding the Mitsunobu reaction at the hydroxyl function.

The desired method essentially can be transferred from solution to solid phase systems by utilizing an oxime unit linked to a support via a linker.

The radical coupling methodology also can employ a bifunctional unit, as depicted in FIG. 5. Thus, coupling between an oxime linked to a support and the bifunctional unit under the described conditions will provide a hydroxylamino linked molecule. This compound can be alkylated in a standard manner to yield a N-substituted molecule. Subsequently, deblocking of the phthalimido group with methyl hydrazine liberates a free O-amino group, which on treatment with formaldehyde gives a terminal oxime. The oxime can be used in another round of coupling with an iodo derivative. In this manner the synthesis is more convenient, due to the Mitsunobu reaction prior to coupling. Radical coupling cycles can be repeated as often as needed until a polymer of desired length is obtained. The elongation usually is terminated by using a last unit, as shown in FIG. 5, that bears a protected hydroxyl group. The foregoing procedure is highly adaptable to solution phase chemistry in a similar manner.

EXAMPLE 1

Reductive Coupling

I. Solution phase Synthesis of an Oligomeric Molecule Linked Via Hydrazino Linkages (FIG. 1)

A. Synthesis of a 'First Unit', 1-O-(t-butyldiphenylsilyl)-butyraldehyde-1-ol, 3 ($R_Z$=t-butyldiphenylsilyl (TBDPS), r=1)

A mixture of 4-penten-1-ol (10 mmol), t-butyldiphenylsilylchloride (12 mmol), imidazole (25 mmol) and dry DMF (50 ml) is stirred at room temperature for 16 h under argon. The reaction mixture is poured into ice-water (200 ml) and the solution extracted with $CH_2Cl_2$ (2×200 ml). The organic layer is washed with water (2×200 ml) and dried ($MgSO_4$). The $CH_2Cl_2$ layer is concentrated to furnish a gummy residue, which on purification by silica gel chromatography gives silylated 4-penten-1-ol. The silylated compound is oxidized with $OsO_4$ (1 mmol) and N-methylmorpholine oxide (20 mmol) in diethyl ether (40 ml) and water (20 ml) at room temperature for 18 h. $NaIO_4$ (30 mmol) solution in water (2 ml) is added to the above solution and stirring is continued for 12 h. The aqueous layer is extracted with diethyl ether (2×200 ml) and evaporation of combined organic layers gives crude aldehyde 3.

B. Synthesis of a 'Bifunctional Units', 4-Penten-1-hydrazine hydrochloride, 8, and Imidazolidine Derivative, 5

Treatment of 4-Penten-1-ol with tosylchloride in pyridine will furnish tosylated 6, which on treatment with benzylcarbazate in dimethylacetamide as described in Example 1 of Ser. No. 08/039,979, filed Mar. 30, 1993, now abandoned, provides the carbazyl derivative 7. Hydrogenation with Pd/C in MeOH/HCl provides the title compound 8 as hydrochloride salt.

The aldehyde group of 3 is protected as N,N'-diphenylimidazolidine derivative utilizing the procedure of Giannis, et. al., *Tetrahedron* 1988, 44, 7177, to furnish 4. Subsequently, 4 is treated with $Bu_4NF$/THF to deblock the silyl protecting group. The hydroxyl group of the latter compound is transformed into a hydrazino group via the two step procedure described above to yield title compound 5.

C. Synthesis of a 'Terminal Unit', 3-O-(t-butyldiphanylsilyl)-1-(hydrazine)-propanol hydrochloride (11, $R_Z$=TBDPS, r=1).

The title compound is prepared from propane-1,3-diol, via selective silylation with t-butyldiphenylsilylchloride, followed by treatment with benzylcarbazate and hydrogenation as described above in Example 1(I)(B).

D. Solution Phase Coupling of a 'First Unit' and a 'Bifunctional Unit'

Aldehyde 3 and hydrazino derivative 8 are coupled in dry $CH_2Cl_2$/MeOH/AcOH as described in Example 3 of Ser. No. 08/039,979, filed Mar. 30, 1993, to furnish an intermediate hydrazone 9 ($L_S$=CHO). The latter product is reduced with $NaBH_3CN$/AcOH to furnish a hydrazino linked molecule 10 ($L_S$=N,N'-diphenylimidazolidino). Subsequently, 10 is bis-alkylated with N1-methylformylthymine to yield 12 ($R_Z$=H, $L_S$=$CH_2OH$, $R_Y$=N1-ethylthymine).

The reactive aldehyde moiety of 12 can be regenerated by acid treatment to deblock the N,N-diphenyl imidazolidine. If compound 5 is used in place of compound 8, the aldehyde moiety can be regenerated by $OsO_4$ oxidation/$NaIO_4$ cleavage of the terminal vinyl moiety (i.e., $L_S$=CH=CH2). Thus, another round of coupling is carried out followed by reduction and alkylation with tether or tether plus a new ligand. In this manner, one can place a variety of ligands on a single molecule, separated by an appropriate linear chain, an important feature for recognition of macromolecules.

The coupling may be terminated at any point by utilizing a terminal unit, such as molecule 11. This compound provides a hydrazino end to couple with an aldehyde but bears a protected hydroxyl group, which will be deblocked to provide an hydroxyl moiety.

In addition, one may choose to attach a phosphate or phosphonate group via terminal hydroxyl group in order to provide higher solubility to oligomeric unit.

II. Automated Solid Support Synthesis of an Oligomeric Molecule Linked Via Hydrazino Linkages (FIG. 1)

A. Synthesis of a 4-Penten-1-ol Attached to Solid Support

4-Penten-1-ol is attached via a succinyl linker onto CPG following standard protocol (e.g., R. T. Pon in Protocols For Oligonucleotides And Analogs, Chapter 24, Agrawal, S., ed., Humana Press, Totowa, N.J., 1993.). The CPG bound 4-penten-1-ol 2 ($R_Z$=CPG, r=1) is oxidized with $OsO_4$, and the product treated with $NaIO_4$ to yield 3 with a free aldehydo group. Next, a reductive coupling with bifunctional unit such as 5 furnishes 10 bound on CPG. Subsequent alkylation with a tether such as chloroethane furnishes 12. In a similar manner, the deblocking of imidazolide with acid and repeated coupling with another bifunctional unit allows the linear growth of the hydrazino linked oligomer, until a desired length of the molecule is obtained.

The foregoing solid support synthesis can be transferred to a robotic or automated synthesis technology as, for example, in the generation and rapid screening of libraries of molecules (see, e.g., Zuckermann, et. al., *J. Am. Chem. Soc.* 1992, 116, 10646).

EXAMPLE 2

Reductive Coupling

Figure 2:
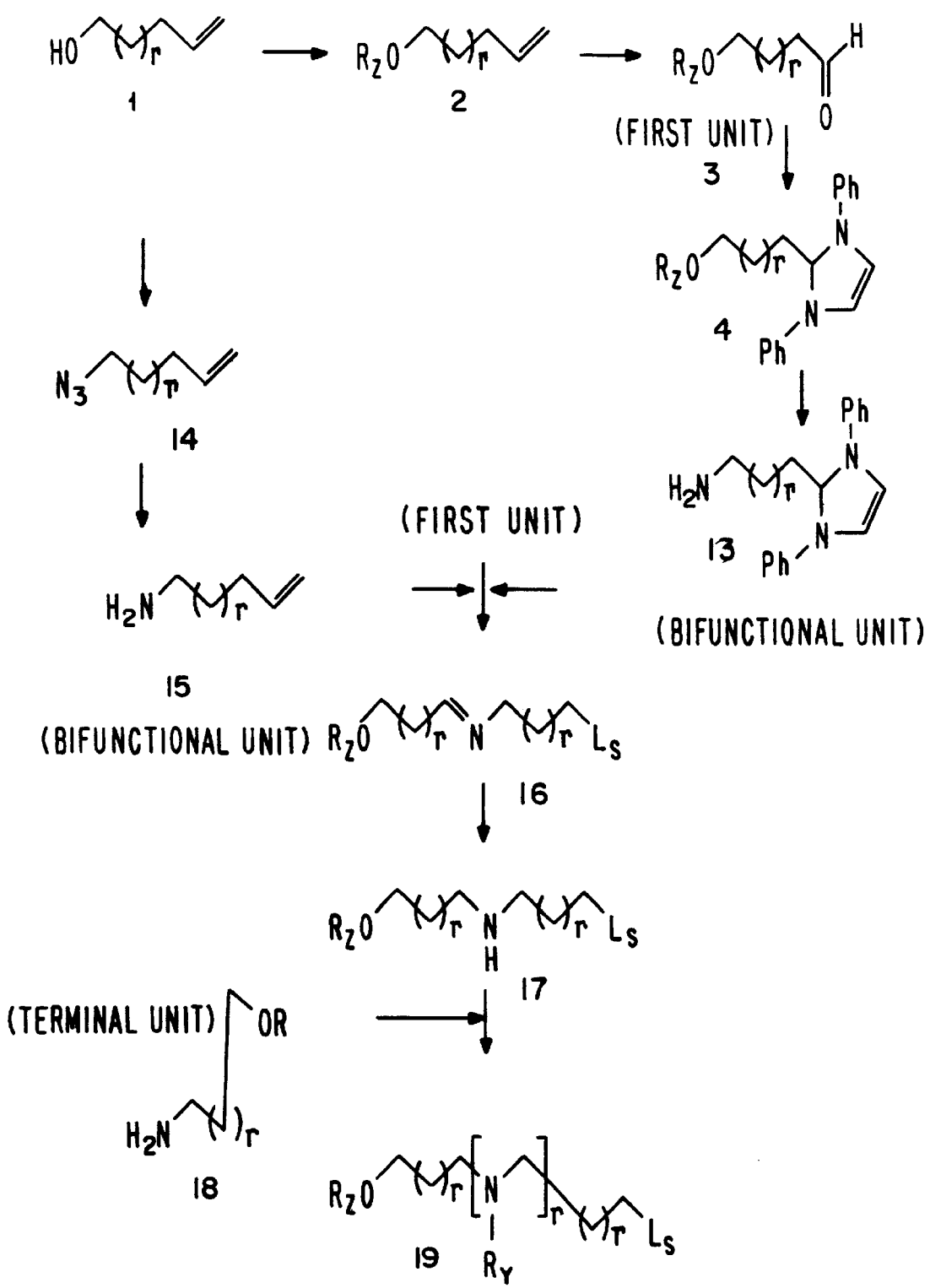
FIG. 2 shows solid phase and solution phase processes for synthesis of amino-linked compounds according to the invention.

Solution Phase Synthesis of Oligomeric Molecule Linked Via Amino Linkages (FIG. 2)

The 'first unit' for this synthesis is the same as used in Example 1, above.

A. Synthesis of Bifunctional Units, 4-Pentenyl-1-amine, 15, and 3-(N,N-diphenyl imidazolidine)-butyl-1-amine, 13.

Treatment of 4-penten-1-ol 1 (r=1) with methlysulfonyl chloride in pyridine at 0° C. affords the sulfonate, which on treatment with lithium azide in DMF gives azido derivative 14. Reduction of 14 with tributyltin hydride in dimethyl acetamide furnishes title compound 15.

Yet another bifunctional unit 13 is prepared in five steps, starting from 1. The hydroxyl group initially is protected with t-butyldiphenyl silyl group and the product, on oxidative cleavage using $OsO_4$/$NaIO_4$, gives aldehyde 3 ($R_Z$=TBDPS). The latter compound is further transformed to the imidazolidine derivative 4, which on desilylation followed by conversion of the hydroxyl group to an amino group via an azide, furnishes 13 (see, e.g., Lin, et. al., *J. Med. Chem.* 1978, 21, 109).

B. Coupling of First and Bifunctional Units

To a stirred solution of aldehyde 3, amine 13 and acetic acid in $CH_2Cl_2$ is added $NaBH(OAc)_3$ under argon. Alternatively, amine 15 is used in place of amine 13. The suspension is stirred for 3 h and the reaction mixture, on work up as described in Example 17 of Ser. No. 08/039,979, filed Mar. 30, 1993, now abandoned, gives the dimeric 17 ($L_S$=CHO or CH=$CH_2$). Reductive amination is performed thereon generally in accordance with *Tet. Lett.,* 1990, 31, 5595. Subsequently, the amino functionality is reductively alkylated with N1-methylformylthymine to provide 19 ($R_Z$=H, $L_S$=$CH_2OH$, $R_Y$=N1-ethylthymine). Coupling can be repeated to obtain compounds of formula 19 with varying length (e.g. r=1–20).

EXAMPLE 3

Nucleophilic Coupling

Figure 3:
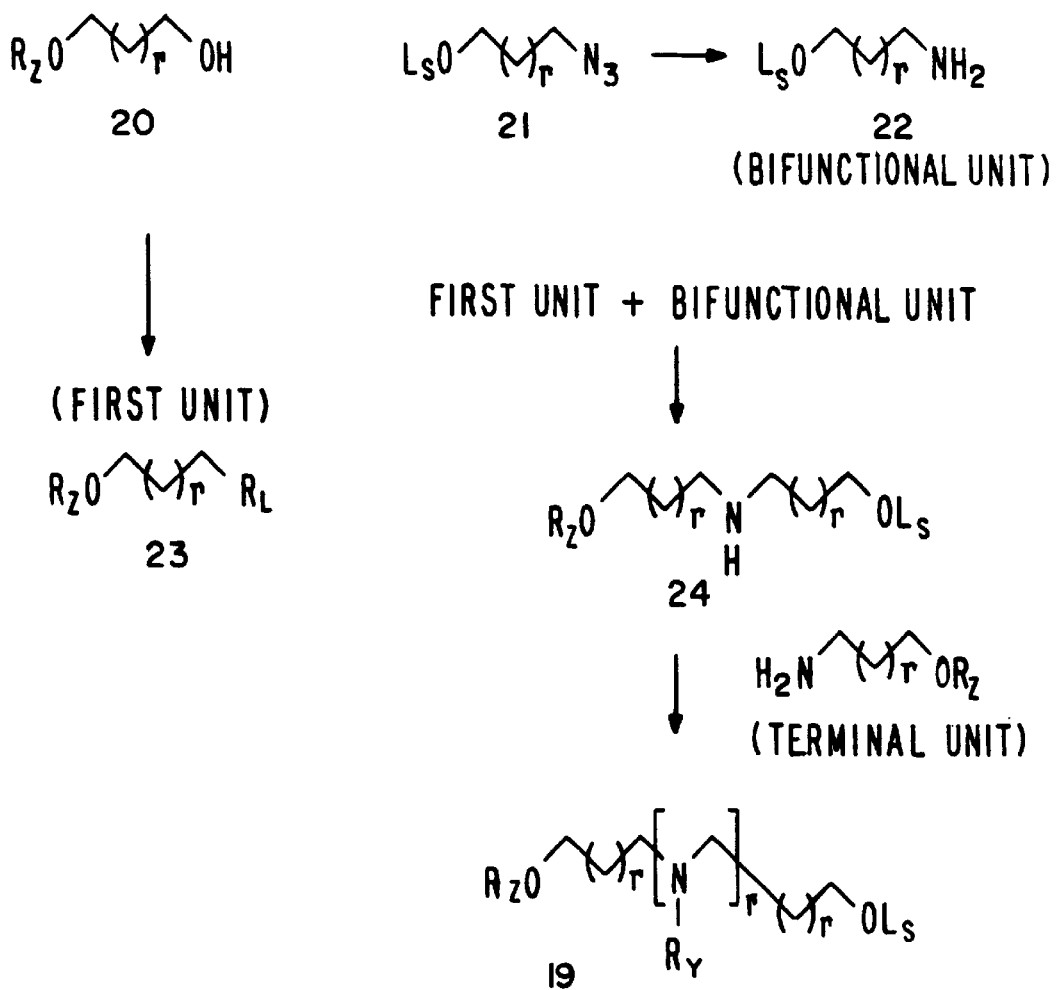
FIG. 3 shows further solid phase and solution phase processes for synthesis of amino-linked compounds according to the invention.

Oligomeric Molecules Linked Via Amino Linkages (FIG. 3)

FIG. 3 describes a general method for assembly of amino linked linear molecules. Further methods are described by Niitsu, et. al., *Chem. Pharm. Bull.* 1986, 31, 1032.

A. Synthesis of First Unit, 23

The title compound is prepared from commercial 1, 3-propanediol, which on monosilylation with t-butyldiphenylsilylchloride gives protected 20 ($R_Z$=TBDPS, r=1). The free hydroxyl group of 20 is then converted into a tosyl leaving group as described by J. March in Advanced Organic Chemistry, Reactions, Mechanisms, and Structure, page 352, John Wiley & Sons, New York, 1992 to furnish 23 ($R_L$=O-tosyl). Other suitable leaving groups include brosylates, nosylates, mesylates or halides.

B. Synthesis of Bifunctional Unit, 22

Treatment of 3-bromo-1-propanol with lithium azide in DMF furnishes 3-azido-1-propanol, which on silylation provides 21 ($L_S$=TBDPS, r=1). The azido group of 21 is reduced to provide the bifunctional unit 22. The nitrogen nucleophile at the reactive end of compound 22 is blocked with a 9-fluorenylmethoxycarbonyl (FMOC) group, and the hydroxyl group at the dormant end is deblocked and transformed into a reactive ester as in Example 3(A), above to provide 23 ($L_S$=tosyl).

C. Coupling of First Unit and Bifunctional Unit

Compounds 22 and 23 are reacted in presence of an appropriate base to furnish a secondary amine 24 as the product. Subsequently, amino group of 24 is reductively alkylated with N1-methylformylthymine to yield compound 19 ($R_Z$=H, $L_S$=H, $R_Y$=N1-ethylthymine). In order to continue with coupling, the blocking group from hydroxyl moiety is removed and the resulting hydroxyl group connected to an active ester moiety. Another round of coupling takes place, followed by alkylation/deblocking/esterification steps until a molecule of desired length is obtained.

EXAMPLE 4

Reductive Coupling

Solution Phase Synthesis of an Oligmeric Molecule Linked Via Hydroxylamine Linkages (FIG. 4)

A. Synthesis of a 'First Unit', Amino-O-benzylalcohol, 27

Title compound 27 is prepared in two steps starting from commercial benzyl alcohol 25 ($L_S$=phenyl). In the first step, Mitsunobu reaction of 25 with N-hydroxyphthalimide/triphenylphosphine/diethylazodicarboxylate gives an o-phthalimido derivative 26. Treatment of 26 with methylhydrazine gives 27.

B. Synthesis of a 'Bifunctional Unit', 3

Title compound 3 is prepared in a manner described in Example 1, above.

C. Coupling of a 'First Unit' and a 'Bifunctional Unit'

A mixture of 27, 3, and acetic acid is stirred in $CH_2Cl_2$ for 1 h at room temperature. The solvent is evaporated to furnish the crude oxime 28, which on reduction with $NaBH_3CN$/AcOH (as described in Example 11 of Ser. No. 08/039,979, filed Mar. 30, 1993, now abandoned,) furnishes 29. The amino group of 29 is further reductively alkylated with N1-methylformylthymine to yield 30 ($R_Z$=H, $L_S$=phenyl, $R_Y$=N1-ethylthymine).

Alternatively, the terminal phthalimido group of 28 is deblocked with 3% methylhydrazine in $CH_2Cl_2$ and the o-amino group is coupled with another bifunctional unit under acidic conditions. This cycle of treatment can be repeated with methylhydrazine and coupling until an oligomer of desired length is formed. All oxime linkages can be reduced in one step using $NaBH_3CN$/AcOH treatment, as described above. A common tether or a tether and ligand then can be attached in a single alkylation step to yield 30. However, this methodology provides a means to obtain an oligomeric unit with similar tether or tether and ligand placed onto amino group.

In another method, the oxime linkage is reduced immediately after coupling and attachment of the tether or tether and ligand is effected. This modification in the procedure allows placement a tether or tether and ligand of choice at a preselected position within an oligomer.

EXAMPLE 5

Radical Coupling

I. Solution Phase Radical Coupling Methodology for Linear Hydroxylamino Linked Oligomers (FIG. 5)

A. Synthesis of a 'First Unit', O-Benzylformaldoxime, 31 ($L_S$=phenyl)

The title compound is prepared from benzyl alcohol following a procedure generally in accordance with Hart, et. al., *J. Am. Chem. Soc.* 1988, 110, 1631.

B. Synthesis of Bifunctional Unit, 2-Iodo-1-O-phthalimidoethanol, 33

Ethyleneglycol is selectively protected with t-butyldiphenylsilyl group generally in accordance with Nair, et. al., *Org. Prep. Procedures Int.* 1990, 22, 57. A Mitsunobu reaction of the monosilylated ethyleneglycol with N-hydroxyphthalimide in a manner described by Debart, et. al., *Tet. Lett.* 1992, 33, 2645, furnishes 2-O-tert-butyldiphenylsilyl-1-O-phthalimidoethanol. Deblocking of the silyl group of this compound with $Bu_4NF$/THF, followed by iodination provides the desired bifunctional molecule 33.

C. Coupling of a 'First Unit' and a 'Bifunctional Unit'

Bis(trimethyltstannyl)benzopinacolate mediated intermolecular free-radical carbon-carbon bond-forming reaction is carried out in benzene generally in accordance with Example 85 of Ser. No. 08/039,979, filed Mar. 30, 1993, now abandoned, with 31 as a radical acceptor and 33 as a radical precursor to yield a linear hydroxylamine 29 ($R_Z$=Phth.).

The amino group of hydroxylamine 29 is reductively alkylated with N1-methylformylthymine to yield 30 ($R_Z$=Phth., $R_Y$=N1-ethylthymine). Treatment of 30 with 3% methylhydrazine/$CH_2Cl_2$ provides a terminal O-amino group, which on formylation with 1 mol equivalent of HCHO/MeOH provides an oxime functionality at the reactive end of 30 ($R_Z$=N=$CH_2$) for the next round of coupling. Thus, the chain length is extended by reacting 30 with 33 in a similar manner, followed by alkylation, hydrazinolysis and formylation to obtain the desired length of the oligomer. The final, terminal unit 32 is employed when no more chain elongation is required. Deblocking with $Bu_4NF$ will furnish a terminal hydroxyl group in oligomeric 30.

II. Solid Support Synthesis

As described in Example 1(II)(A), above, oligomeric molecules are prepared by attaching 31 ($L_S$=$CH_2OH$) to a solid support such as CPG or polystyrene via an appropriate linker. Once the oligomer of desired length is obtained, the product is cleaved from the support to furnish fully deblocked product, 30.

EXAMPLE 6

Reductive Coupling
Solid Support Synthesis of Covalently Linked Duplex Structures as Hairpins/Stem-Loops and Cyclic Oligomeric Structures Via Hydroxylamino Linkages (FIG. 6)

A. Cyclic Oligomers

An appropriate solid support, such as 35 (Y=phenyl) is prepared from trisubstituted benzene following a double Mitsunobu reaction described in *Tet. Lett.* 1992, 33, 2645 and loading of the product via succinyl linker (Z) onto a CPG support (see, e.g., R. T. Pon in Protocols For Oligonucleotides And Analogs, Chapter 24, Agrawal, S., ed., Humana Press, Totowa, N.J., 1993.). The CPG bound material is packed into a 1 µM column and attached to an ABI DNA synthesizer 380 B model. Bis-phthalimido groups are deblocked with 3% N-methyl hydrazine/$CH_2Cl_2$ solution to liberate desired bis-O-amino moiety, 35. Then, bifunctional reagent 3 ($R_Z$=TBDPS) is employed with 5% AcOH/$CH_2Cl_2$ to give bis-oxime 38 (r=1). Deblocking with N-methyl hydrazine and coupling with 3 is repeated until an oligomeric bis-oxime of desired length is obtained. The CPG loaded 40 is removed from the synthesizer and treated with ACOH/$NaCNBH_3$ to yield reduced hydroxyl amine 39. Subsequently, all amines are reductively alkylated with N1-methylformylthymine to provide 40 ($R_Y$=N1-ethylthymine). The terminal bis-phthalimido groups of 40 are deblocked with N-methyl hydrazine and final conjugation with bis-aldehyde 37 provides circularized 41, which can be further reduced, alkylated and removed from CPG to yield appropriate circular oligomers, such as 42.

B. Circular/Dumbbelled Oligomers

The method set forth in Example 6(I)(A), above, can be further modified to produce molecules that are constructed as linear strands but that on partial self-hybridization assume defined secondary structures.

Heterobifunctional solid support 36 (Y=phenyl, Z=succinyl, $L_S$=N,N'-diphenyl imidazolidino) is prepared from trisubstituted benzene according to the procedures of Examples 1(I)(A) and 6(I)A). The support bears a protected aldehydo group on one end, a succinyl linker attached to the CPG support on a second end, and an O-amino functionality on a third end. Coupling of 3 with 36 provides oxime 43. The product 43 is reduced with $NaCNBH_3$/EtOH solution, followed by alkylation with N1-methylformylthymine to provide a ligand 40 ($R_Y$=N1-ethylthymine) with hydrogen bonding capacity. Similarly, deblocking with N-methyl hydrazine, followed by coupling with 3, and reductive alkylation provides a linear sequence bearing nucleic acid bases (A,C,G,T) in a defined order. Elongation of this oligomer is terminated when an appropriate length is achieved. The oligomer is detached from the CPG and purified by HPLC. The pure oligomer is able to self-hybridize to provide either circular or dumbbell structures of any length.

C. Hairpin/Stem-Loop Duplexes

In order to prepare partially or fully self-complementary molecules, synthesis is commenced with a molecule bearing two functionalities. One of these functionalities is the reactive end of the molecule and the other remains dormant/protected. Therefore, a heterobifunctional molecule is attached to the CPG to give protected 36, which is deblocked with N-methyl hydrazine to yield 36 with a free O-amino group. As in Example 6(I)(B), above, coupling with 3 in presence of acetic acid provides oxime 43. In two steps, the oxime is reduced and alkylated with an appropriate nucleic acid base (such as A,C,G,T) via a tether to furnish 44. The chain is elongated utilizing a three step process (deblocking, then coupling, then reductive alkylation) until an oligomer of desired length is obtained. Finally, the linear molecule is deblocked from CPG and dissolved in salt-buffer to provide a self complementary secondary structure as per the preorganized nucleic acid bases.

The protected end of the molecule is deblocked and utilized for a site-specific cross-linking on the complementary strand. Such cross-linked molecules are expected to provide additional conformational and structural stability to maintain a duplex hairpin or stem-loop or dumbbelled shape.

EXAMPLE 7

Figure 7A:
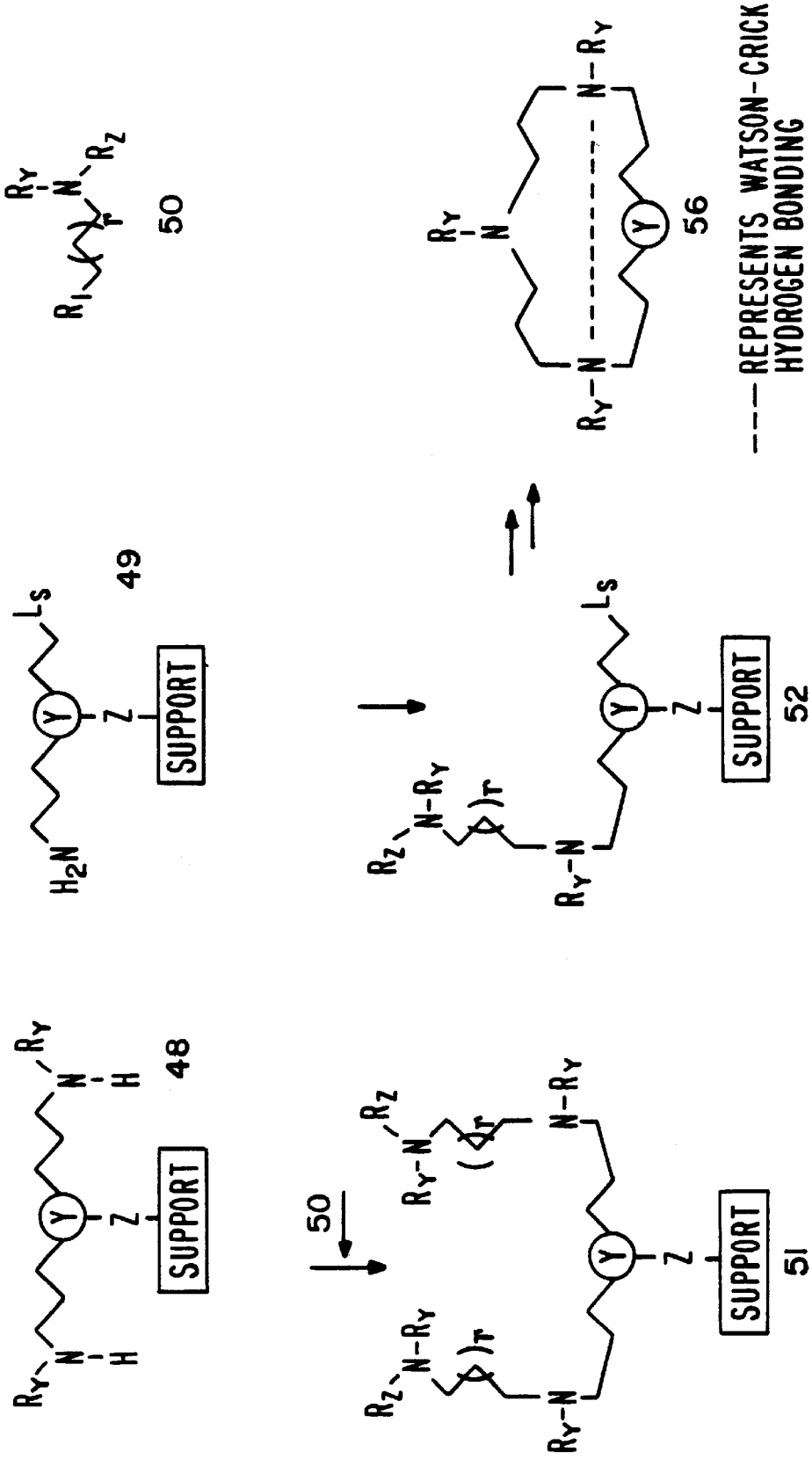
FIG. 7 shows solid phase processes for synthesis of duplex, hairpin, stem-loop, and cyclic amino-linked compounds according to the invention.
Figure 7B:
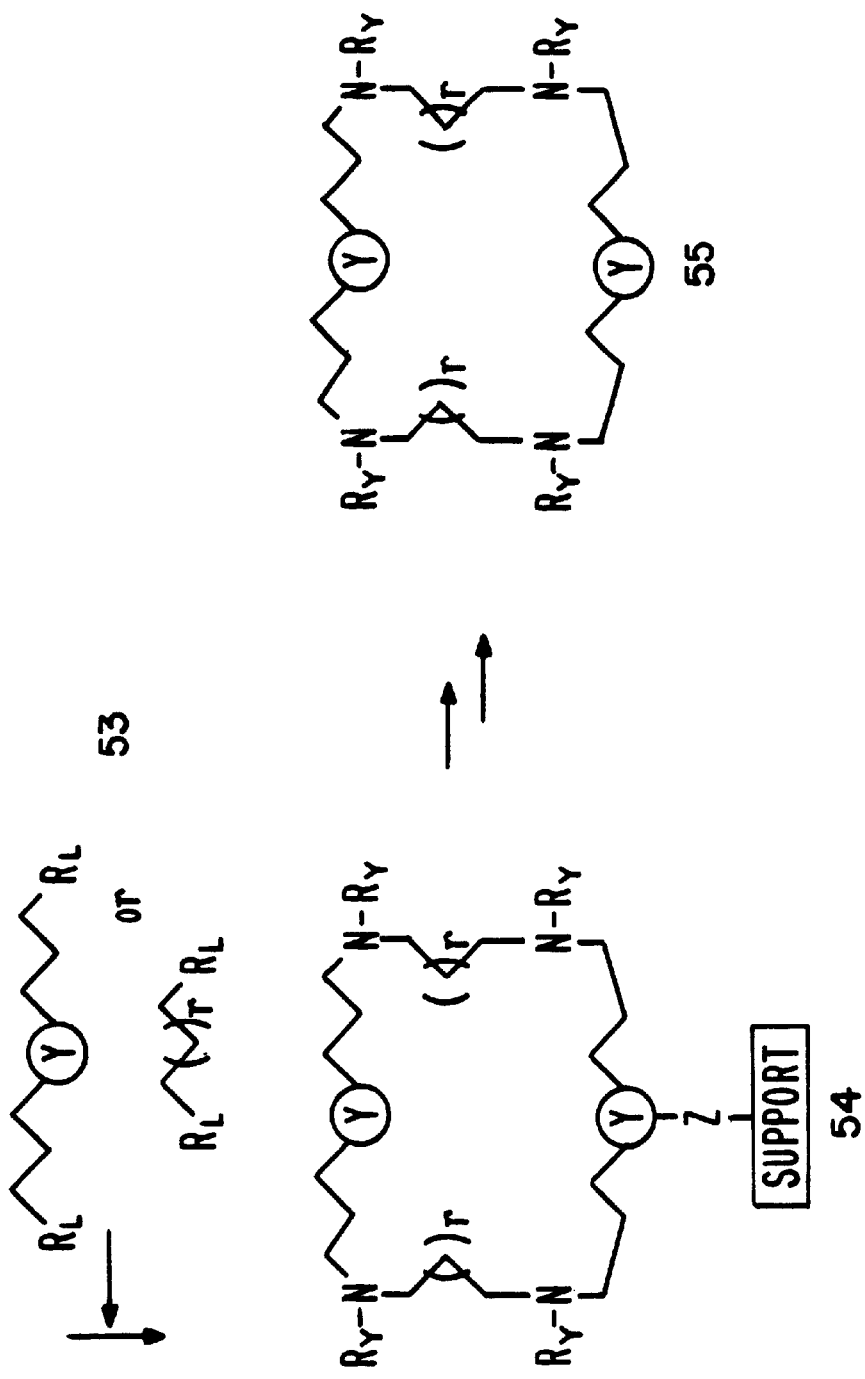

Solid Support Synthesis of Covalently Linked Duplex/Hairpins/Stem-Loops and Cyclic Oligomers Via Amino Linkage FIG. 7 describes one method for assembly of amino linked duplexes or circular oligomers. Tuladhar, et. al., *Tet. Lett.* 1992, 33, 2203, describes a synthetic route for the preparation of poly-N-$N^1$-dimethylethylenediamines, which method can be adapted for preparation of the title oligomers.

A. Circular Polyamine, 55

A bis-N-alkylated phenyl amine bearing a tether, T, and a ligand, L, is conjugated to CPG via standard procedures (see, e.g., R. T. Pon in Protocols For Oligonucleotides And Analogs, Chapter 24, Agrawal, S., ed., Humana Press, Totowa, N.J., 1993.) to provide 48 (Y=phenyl, Z=succinyl, $R_Y$=N1-alkylated pyrimidine bases or N9-alkylated purine bases). A complete set of appropriately alkylated amine building blocks 50 ($R_L$=O-tosyl, $R_Y$=N1-ethylthymine, $R_Z$=FMOC) next are prepared with a leaving group and protected secondary amine at opposite ends. Nucleophilic displacement of the leaving group of 50 by bis-N-alkylated 48 in presence of an appropriate base, such as $K_2CO_3$ or triethylamine results in formation of branched 51. The protecting group of the bis-amino function is removed and yet another round of base catalyzed coupling furnishes a longer oligomer. Thus, repetition of deblocking and coupling provides a molecule of desired length. To close the loop or tie the two amino branched, compound 53 having bis-leaving groups ($R_L$) are employed to provide a circularized oligomer 54. The oligomer is then deblocked from the support in a standard manner (see, e.g., Oligonucleotide Synthesis, Gait, M. J., ed., IRL Press, Oxford, 1984.)

Alternatively, 51 is deblocked after a desired length is achieved to provide a linear oligomer. This oligomer is circularized by template-directed coupling, wherein a short complementary oligomer is employed to hybridize the loose ends and then carry out the coupling with 53 to provide compound 55. Kool, et. al., *J. Chem. Soc. Chem. Commun.* 1991, 1161, have reported similar ligation of reactive ends (utilizing a template) to yield circularized products.

B. Hairpin and Stem-Loops Linked Via Polyamines

As described in Example 6(I)(C), above, self-complementary hairpin and stem-loop structures are prepared in accordance with FIG. 7. Synthesis is accomplished by alkylation of N-alkyl amine 50 ($R_L$=I) with monoamine 49 ($L_S$=N,N'-diphenyl imidazolidino) to furnish 52. Use of an iodo leaving group in 50 is preferred, due to high coupling efficiency. Also preferred is use of a bifunctional reagent 50 which already bears a nucleic acid residue attached via a tether. Thus, it is possible to incorporate appropriate ligands (heterocyclic bases) one at a time to introduce the desired recognition element into the growing oligomer. Once an oligomer of expected length is obtained, it is removed from the support by standard methods.

The oligomer is allowed to anneal under appropriate salt concentrations to provide a hairpin or stem-loop structure. The development of these methods for cationic polyamine synthesis are attractive because their unique interaction with anionic DNA and presence of an active uptake system in a variety of cell types.

EVALUATION

PROCEDURE 1—Nuclease Resistance

A. Evaluation of the resistance of oligonucleotide-mimicking macromolecules to serum and cytoplasmic nucleases.

Compounds of the invention can be assessed for their resistance to serum nucleases by incubation of the oligonucleotide-mimicking macromolecules in media containing various concentrations of fetal calf serum or adult human serum. Labelled compounds are incubated for various times, treated with protease K and then analyzed by gel electrophoresis on 20% polyacrylamine-urea denaturing gels and subsequent autoradiography. Autoradiograms are quantitated by laser densitometry. Based upon the location of the modified linkage and the known length of the oligonucleotide-mimicking macromolecules it is possible to determine the effect on nuclease degradation by the particular modification. For the cytoplasmic nucleases, an HL 60 cell line can be used. A post-mitochondrial supernatant is prepared by differential centrifugation and the labelled compounds are incubated in this supernatant for various times. Following the incubation, compounds are assessed for degradation as outlined above for serum nucleolytic degradation. Autoradiography results are quantitated for evaluation of the macromolecules of the invention. It is expected that the compounds of the invention will be completely resistant to serum and cytoplasmic nucleases.

B. Evaluation of the resistance of oligonucleotide-mimicking macromolecules to specific endo- and exo-nucleases.

Evaluation of the resistance of natural oligonucleotides and compounds of the invention to specific nucleases (i.e., endonucleases, 3',5'-exo-, and 5',3'-exonucleases) can be done to determine the exact effect of the macromolecule linkage on degradation. The compounds are incubated in defined reaction buffers specific for various selected nucleases. Following treatment of the products with protease K, urea is added and analysis on 20% polyacrylamide gels containing urea is done. Gel products are visualized by staining with Stains All reagent (Sigma Chemical Co.). Laser densitometry is used to quantitate the extent of degradation. The effects of the compound's linkage are determined for specific nucleases and compared with the results obtained from the serum and cytoplasmic systems. As with the serum and cytoplasmic nucleases, it is expected that the compounds of the invention will be completely resistant to endo- and exo-nucleases.

PROCEDURE 2—5-Lipoxygenase Analysis and Assays

A. Therapeutics

For therapeutic use, an animal suspected of having a disease characterized by excessive or abnormal supply of 5-lipoxygenase is treated by administering a compounds of the invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The compounds of this invention will also be useful as research reagents when used to cleave or otherwise modulate 5-lipoxygenase mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 Mg of total RNA in a buffer consisting, for example, of 50 mm phosphate, pH ranging from about 4–10 at a temperature from about 30° to about 50° C. The cleaved 5-lipoxygenase RNA can be analyzed by agarose gel electrophoresis and hybridization with radiolabeled DNA probes or by other standard methods.

C. Diagnostics

The compounds of the invention will also be useful in diagnostic applications, particularly for the determination of the expression of specific mRNA species in various tissues or the expression of abnormal or mutant RNA species. In this example, while the compounds target a abnormal mRNA by being designed complementary to the abnormal sequence, they would not hybridize to normal mRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which is cleaved, would not be bound to the support and therefore would be separated from the normal mRNA.

Targeted mRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte like cell or neutrophil like cell by various known agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of oligonucleotide-mimicking compounds which interfere with 5-lipoxygenase synthesis in these cells.

A second test system for oligonucleotide-mimicking compounds makes use of the fact that 5-lipoxygenase is a "suicide" enzyme in that it inactivates itself upon reacting with substrate. Treatment of differentiated HL-60 or other cells expressing 5 lipoxygenase, with 10 µM A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Compounds directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

A direct effect which oligonucleotide-mimicking compounds can exert on intact cells and which can be easily be quantitated is specific inhibition of 5-lipoxygenase protein synthesis. To perform this technique, cells can be labelled with $^{35}S$-methionine (50 µCi/mL) for 2 hours at 37° C. to label newly synthesized protein. Cells are extracted to solubilize total cellular proteins and 5-lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 µM, 10 µM, and 30 µM of the compounds of the invention for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 µM $^{14}C$-arachidonic acid, 2 mM ATP, 50 µM free calcium, 100 µg/ml phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective the macromolecules of the invention at 1 µM, 10 µM, and 30 µM would be as follows. Control cells oxidize 200 pmol arachidonic acid/5 min/106 cells. Cells treated with 1 µM, 10 µM, and 30 µM of an effective oligonucleotide-mimicking compound would oxidize 195 pmol, 140 pmol, and 60 pmol of arachidonic acid/5 min/106 cells respectively.

A quantitative competitive enzyme linked immunosorbant assay (ELISA) for the measurement of total 5-lipoxygenase protein in cells has been developed. Human 5-lipoxygenase expressed in *E. coli* and purified by extraction, Q-Sepharose, hydroxyapatite, and reverse phase HPLC is used as a standard and as the primary antigen to coat microtiter plates. Purified 5-lipoxygenase (25 ng) is bound to the microtiter plates overnight at 4° C. The wells are blocked for 90 min with 5% goat serum diluted in 20 mM Tris·HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 µL in the microtiter wells for 90 min. The antibodies are prepared by immunizing rabbits with purified human recombinant 5-lipoxygenase. The wells are washed with TBS containing 0.05% tween 20 (TBST), then incubated with 100 µL of a 1:1000 dilution of peroxidase conjugated goat anti-rabbit IgG (Cappel Laboratories, Malvern, Pa.) for 60 min at 25° C. The wells are washed with TBST and the amount of peroxidase labelled second antibody determined by development with tetramethylbenzidine.

Predicted results from such an assay using a 30 mer oligonucleotide-mimicking compound at 1 µM, 10 µM, and 30 µM would be 30 ng, 18 ng and 5 ng of 5-lipoxygenase per $10^6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into a neutrophil-like cell. Cells (2×10$^5$ cells/mL) will be treated with increasing concentrations of the macromolecule for 48–72 hours in the presence of 1.3% DMSO. The cells are washed and resuspended at a concentration of 2×10$^6$ cell/mL in Dulbecco's phosphate buffered saline containing 1% delipidated bovine serum albumin. Cells are stimulated with 10 µM calcium ionophore A23187 for 15 min and the quantity of LTB4 produced from 5×10$^5$ cell determined by radioimmunoassay as described by the manufacturer.

Using this assay the following results would likely be obtained with an oligonucleotide-mimicking compound directed to the 5-LO mRNA. Cells will be treated for 72 hours with either 1 µM, 10 µM or 30 µM of the macromolecule in the presence of 1.3% DMSO. The quantity of $LTB_4$ produced from 5×10$^5$ cells would be expected to be about 75 pg, 50 pg, and 35 pg, respectively with untreated differentiated cells producing 75 pg $LTB_4$.

E. In Vivo Assay

Inhibition of the production of 5-lipoxygenase in the mouse can be demonstrated in accordance with the following protocol. Topical application of arachidonic acid results in the rapid production of leukotriene $B_4$, leukotriene $C_4$ and prostaglandin $E_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Compounds of the invention are applied topically to both ears 12 to 24 hours prior to administration of arachidonic acid to allow optimal activity of the compounds. Both ears are pre-treated for 24 hours with either 0.1 μmol, 0.3 μmol, or 1.0 μmol of the macromolecule prior to challenge with arachidonic acid. Values are expressed as the mean for three animals per concentration. Inhibition of polymorphonuclear cell infiltration for 0.1 μmol, 0.3 μmol, and 1 μmol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

P. Hybridization Probes.

Multiple varieties of mRNA can be quantitated without the need to purify the mRNA from cellular components by first a compound of the invention that hybridizes to the mRNA. The compound then is immobilized on an insoluble solid support such as CPG (see, e.g., R. T. Pon in Protocols for oligonucleotides and Analogs, pages 465–496, S. Agrawal, ed., Humana Press, Totowa, N.J., 1993). The sample under investigation then is incubated with the insoluble CPG support so that the mRNA present in the sample will hybridize to and become immobilized on the CPG support. Non-immobilized materials and components are washed off with suitable media and mRNA on the support then is labelled with ethidium bromide, biotin or a commercial radionucleotide. Measurement of the amount of label immobilized on the CPG support will indicate the amount of mRNA present in the starting sample. Such measurement will provide an indication of the pathophysiology of a disease state associated with the mRNA.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for forming a covalent linkage comprising the steps of (a) providing synthons having structures:

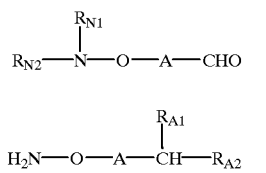

(b) contacting said synthons for a time and under reaction conditions effective to form a covalent linkage having formula —CH=N—;

wherein:

$R_{N1}$ and $R_{N2}$ are, independently, amine protecting groups, or together form an amine protecting group; and $R_{A1}$ and $R_{A2}$ are, independently, hydrogen, aryl, a protected carbonyl, or a group having the formula: $\{N(R_N)-O-A-CH_2\}_r$ where r is 1–100;

each A is, independently, $R_S-X(T-L)-R_S$; $N-R_N$; C(O); a single bond; or $(CH_2)_m$ where m is 1–5;

each $R_N$ is, independently, H, an amine protecting group or T—L;

each $R_S$ is, independently, a single bond or alkyl having 1 to about 12 carbon atoms;

each T is, independently, a single bond, a methylene group or a group having structure II:

$$-[CR^1R^2]_n-B-[CR_1R_2]_o-[D]_p-[N(R_N)]_q-$$
II where:

D is C(O), C(S), C(Se), $C(R^1)(N^3R^4)$, $CH_2R^1$, $CHR^1R^2$, or $NR^3R^4$;

B is a single bond, CH=CH, C≡C, O, S or $NR^4$;

each $R^1$ and $R^2$ is independently selected from the group consisting of hydrogen, alkyl or alkenyl having 1 to about 12 carbon atoms, hydroxy- or alkoxy- or alkylthio-substituted alkyl or alkenyl having 1 to about 12 carbon atoms, hydroxy, alkoxy, alkylthio, amino and halogen;

$R^3$ and $R^4$, independently, are H, —T—L, alkyl having 1 to about 10 carbon atoms; alkenyl having 2 to about 10 carbon atoms; alkynyl having 2 to about 10 carbon atoms; aryl having 7 to about 14 carbon atoms; heterocyclic; a reporter molecule; or an RNA cleaving group; or $R^3$ and $R^4$, together, are cycloalkyl having 3 to about 10 carbon atoms or cycloalkenyl having 4 to about 10 carbon atoms;

n and o, independently, are zero to 5;

q is zero or 1;

p is zero to about 10;

each L is, independently, a nucleosidic base, an amino acid side chain, an aromatic hydrocarbon, a heterocycle moiety containing nitrogen, sulfur, and/or oxygen; a carbohydrate, a drug, a reporter molecule; an RNA cleaving group; and each X is, independently, N or CH, or X and T, together, form an aromatic moiety, a pentose, a hexose, or a deoxy derivative of a pentose or a hexose.

\* \* \* \* \*